(12) United States Patent
Gallo et al.

(10) Patent No.: US 11,382,890 B2
(45) Date of Patent: *Jul. 12, 2022

(54) PREVENTION OF ROSACEA INFLAMMATION

(71) Applicant: The Regents of the University of California, Oakland, CA (US)

(72) Inventors: Richard L. Gallo, San Diego, CA (US); Anna Di Nardo, La Jolla, CA (US); Yumiko Muto, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/576,730

(22) Filed: Sep. 19, 2019

(65) Prior Publication Data

US 2020/0215023 A1    Jul. 9, 2020

Related U.S. Application Data

(62) Division of application No. 15/726,069, filed on Oct. 5, 2017, now abandoned, which is a division of application No. 14/774,892, filed as application No. PCT/US2014/025069 on Mar. 12, 2014, now Pat. No. 9,801,848.

(60) Provisional application No. 61/780,758, filed on Mar. 13, 2013.

(51) Int. Cl.
| | |
|---|---|
| *A61K 31/352* | (2006.01) |
| *A61K 9/00* | (2006.01) |
| *A61K 45/06* | (2006.01) |
| *A61K 31/277* | (2006.01) |
| *A61K 31/4741* | (2006.01) |
| *A61K 31/519* | (2006.01) |

(52) U.S. Cl.
CPC .......... *A61K 31/352* (2013.01); *A61K 9/0014* (2013.01); *A61K 31/277* (2013.01); *A61K 31/4741* (2013.01); *A61K 31/519* (2013.01); *A61K 45/06* (2013.01)

(58) Field of Classification Search
CPC .................................................. A61K 31/352
USPC ................................................... 514/259.41
See application file for complete search history.

(56) References Cited

U.S. PATENT DOCUMENTS

| | | | | |
|---|---|---|---|---|
| 7,078,048 B2* | 7/2006 | Kang | ...................... | A61P 27/02 424/401 |
| 7,105,172 B1* | 9/2006 | Bolla | ...................... | A61K 31/74 424/400 |
| 7,429,575 B2 | 9/2008 | Yu | | |
| 7,776,844 B2 | 8/2010 | Yu | | |
| 9,067,969 B2 | 6/2015 | Yu | | |
| 9,801,848 B2* | 10/2017 | Gallo | ................... | A61K 9/0014 |
| 2004/0220259 A1* | 11/2004 | Yu | ......................... | A61K 31/70 514/460 |
| 2006/0074108 A1* | 4/2006 | Gupta | .................. | A61K 31/401 514/332 |
| 2006/0115480 A1* | 6/2006 | Hillman | ................... | A61P 1/00 424/146.1 |
| 2007/0207222 A1* | 9/2007 | Yu | ......................... | A61K 47/14 424/725.1 |
| 2009/0318534 A1 | 12/2009 | Gallo et al. | | |
| 2010/0093827 A1* | 4/2010 | Yu | ......................... | A61K 35/04 514/423 |
| 2011/0287040 A1* | 11/2011 | Maione | .................. | A61P 37/00 424/185.1 |
| 2012/0184493 A1* | 7/2012 | Hutchinson | ............ | A61K 47/32 514/18.6 |
| 2012/0322829 A1* | 12/2012 | Safonova | ................ | A61P 27/02 514/334 |

FOREIGN PATENT DOCUMENTS

WO    WO 92/06706    *    4/1992    ............. A61K 37/64

OTHER PUBLICATIONS

Yamasaki, Nature Medicine, 2007, 13(8), 975-980.*
Reinholz, Annals of Dermatology (2012), 24(2), 126-135.*
Sun, Linchuang Pifuke Zazhi (2013), 42(6), 345-347.*
Kanada, Journal of Investigative Dermatology (2012) 132, 1435-1442.*
Caughey, Immunol Rev. Jun. 2007 ; 217: 141-154.*
Harvima Arch Dermatol Res (2008) 300:461-478.*
Baharlou, Simin., International Preliminary Repod on Patentability and Written Opinion, International Application No. PCT/US14/25069, dated Sep. 24, 2015.
McAleer et al., Rosacea and Neuropeptides, pp. 621-626, C.C. Zouboulis et al. (eds.) Pathogenesis and Treatment of Acne and Rosacea, 621 Springer-Verlag Berlin Heidelberg 2014.
Muto et al., Journal of Investigative Dermatology (2014) 134, 2728-2736.
Young, Lee W., International Search Report and Written Opinion, International Application No. PCT/US14/25069, dated Jun. 16, 2014.

* cited by examiner

*Primary Examiner* — Nizal S Chandrakumar
(74) *Attorney, Agent, or Firm* — Gavrilovich, Dodd & Lindsey LLP

(57) ABSTRACT

The disclosure demonstrates the role of mast cell stabilizers in treating *rosacea*. The disclosure also shows the role of mast cells, cathelicidin, serine protease and/or vitamin D3 in *rosacea* pathology and the use of antagonists and inhibitors thereof to treat *rosacea*.

13 Claims, 6 Drawing Sheets
Specification includes a Sequence Listing.

PREVENTION OF ROSACEA INFLAMMATION

CROSS REFERENCE TO RELATED APPLICATIONS

This application is a divisional of U.S. application Ser. No. 15/726,069, filed Oct. 5, 2017, which application is a divisional of U.S. application Ser. No. 14/774,892, filed Sep. 11, 2015 (now U.S. Pat. No. 9,801,848), which application is a U.S. National Stage Application filed under 35 U.S.C. § 371 and claims priority to International Application No. PCT/US2014/025069, filed Mar. 12, 2014, which claims priority under 35 U.S.C. § 119 from Provisional Application Ser. No. 61/780,758, filed Mar. 13, 2013, the disclosures of which are incorporated herein by reference.

TECHNICAL FIELD

The disclosure relates to methods and compositions for treating skin diseases and disorder and more specifically to methods and compositions for treating *rosacea*.

BACKGROUND

*Rosacea* is a chronic skin condition characterized by recurrent episodes of flushing, erythema, vasodilation, telangiectasia, edema, papules, pustules, hyperplasia, fibroplasia, itching, burning, pain, and skin tightness. Symptoms of *rosacea* are exacerbated by sun exposure, hot weather, immersion in hot water, high humidity, sweating, exercise, emotional stress, and spicy food. The skin condition usually begins between the ages of 30 to 50 and occurs more frequently in women than men.

The etiology of *rosacea* is not well understood, but it has been presumed to be caused by an as yet unidentified infectious agent. Unfortunately, antibiotic administration yields only marginal improvement.

SUMMARY

The disclosure provides methods and composition to treat *rosacea* comprising mast cell stabilizers and/or neuropeptide antagonists.

In one embodiment, the disclosure provides compositions for application to the skin of a subject, the composition comprising a mast cell stabilizer such as cromolyn in an amount effective to block mast cell activation and degranulation.

In another embodiment, the disclosure provide methods to treat a subject having *rosacea* comprising contacting a subject with a mast cell stabilizer or composition comprising a mast cell stabilizer in an amount effective to inhibit mast cell activation or degranulation.

In yet another embodiment, the disclosure provides methods and compositions of either of the foregoing further comprising a serine protease inhibitor (e.g., a kalikrein inhibitor).

In one embodiment, the disclosure provides compositions for application to the skin of a subject, the composition comprising a neuropeptide antagonist in an amount effective to block mast cell activation and degranulation.

In another embodiment, the disclosure provide methods to treat a subject having *rosacea* comprising contacting a subject with a neuropeptide antagonist or composition comprising a neuropeptide antagonist in an amount effective to inhibit mast cell activation or degranulation.

In yet another embodiment, the disclosure provides methods and compositions of either of the foregoing further comprising a serine protease inhibitor (e.g., a kalikrein inhibitor) and/or a mast cell stabilizer.

The disclosure provides a method of treating *rosacea* comprising contacting a subject having *rosacea* with a mast cell stabilizer. In one embodiment, the mast cell stabilizer is selected from the group consisting of lodoxamide, nedocromil, cromolyn, pemirolast and pharmaceutical salts of any of the foregoing. In another embodiment, the method further comprises contacting a subject with an agent that inhibits a neuropeptide. In yet a further embodiment, the method further comprises contacting a subject with serine protease inhibitor. In one embodiment, the serine protease inhibitor inhibits kallikrein SCTE. In another embodiment of any of the foregoing, the method further comprises contacting the subject with a vitamin D3 antagonists. In one embodiment, the neuropeptide is selected from the group consisting of substance P (SP), calcitonin gene-related peptide (CGRP), vasoactive intestinal peptide (VIP), and neurokinin A (NKA). In any of these embodiments, the method results in a reduction or inhibition of matrix metalloprotease activity or expression. In another embodiment, the method results in a reduction of inhibition in the amount of activated LL-37 in the skin. The method can be carried out by topically contacting a subject at a site of *rosacea*.

The disclosure also provides a method of treating *rosacea* comprising contacting a subject having *rosacea* with an agent that inhibits a neuropeptide. In one embodiment, the neuropeptide is selected from the group consisting of substance P (SP), calcitonin gene-related peptide (CGRP), vasoactive intestinal peptide (VIP), and neurokinin A (NKA). In any of these embodiments, the method results in a reduction or inhibition of matrix metalloprotease activity or expression. In another embodiment, the method results in a reduction of inhibition in the amount of activated LL-37 in the skin. The method can be carried out by topically contacting a subject at a site of *rosacea*.

The disclosure also provides a composition comprising a mast cell stabilizer and a second agent selected from the group consisting of: (a) a vitamin D3 antagonist, (b) a serine protease inhibitor, (c) an inhibitor of neuropeptide, and (d) any combination of (a)-(c). In one embodiment, the mast cell stabilizer is selected from the group consisting of lodoxamide, nedocromil, cromolyn, pemirolast and pharmaceutical salts of any of the foregoing. In a further embodiment, the composition is formulated for topical administration.

The disclosure also provide for the use of a mast cell stabilizer in the manufacture of a medicament for the treatment of *rosacea*. In one embodiment, the medicament further comprises a vitamin D3 antagonist. In a further embodiment, the medicament further comprises a serine protease inhibitor. In any of the foregoing embodiments, the mast cell stabilizer is selected from the group consisting of: lodoxamide, nedocromil, cromolyn, pemirolast and pharmaceutical salts of any of the foregoing. In one embodiment, the medicament is formulated for topical administration.

The details of one or more embodiments of the disclosure are set forth in the accompanying drawings and the description below. Other features, objects, and advantages of the disclosure will be apparent from the description and drawings, and from the claims.

Human biopsy samples from healthy and *rosacea* subjects were assessed for chymase and Mmp-9 mRNA expressions (n=6). (b) Photographs of the *rosacea* mouse model. 24 hrs after removal of the hair, the back skins of wild type (C57BL/6) and MC-deficient (KitWsh$^{-/-}$) mice were injected intradermally with 50 μl of 320 μM Cath LL-37 or filtered PBS twice a day for 2 days. Clinical observation was carried out for 72 hours. (c) Skins from WT, WT MC reconstituted KitWsh$^{-/-}$ and KitWsh$^{-/-}$ mice were challenged as indicated and harvested after 72 hours of observation. Mmp-9 mRNA expression in each sample was assessed by RT-PCR. (d) Assessment of MMP protease activities in WT mouse skin following challenge with PBS or the indicated amounts of Cath LL-37. (e) Skin biopsies from WT or KitWsh$^{-/-}$ mice were analyzed by RT-PCR for the expression of MC proteases at 0, 1, 4, and 24 hrs after Cath LL-37 challenge. Statistics: Mann Whitney test, one-way and two-way ANOVA *p<0.05, p<0.01, *p<0.001 (1b-1e: n=3).

FIG. 2A-E shows Cath LL-37 induces mouse MC inflammatory responses. (a) Bone marrow derived mouse MCs were challenged in vitro with 10 ug/mL Cath LL-37 or PBS as indicated. The cells were harvested at different time points and the mRNA was extracted and assessed by RT-PCR for tryptase, chymase and Mmp-9 expression. (b) Cell culture supernatant from bone marrow derived MCs was taken after 24 hrs of Cath LL-37 challenge. MMP and MMP-9 specific activities were measured by assessing cleavage of MMP substrate in the presence or absence of a specific MMP-9 inhibitor, as indicated. (c) Bone marrow derived MCs were treated, as indicated, for 24 hrs before collecting supernatants and assessing degranulation percentage by measuring β-hexosaminidase release. (d) Cultured mouse MCs were challenged with the indicated concentrations of Cath LL-37 for 24 or 48 hrs before supernatants were collected and the amounts of IL-6 secretion were measured. (e) 11-6 mRNA expression was measured by RT-PCR in mouse skin biopsies after 0, 1, 4, and 24 hrs of Cath LL-37 challenge in WT and MC deficient mice, as indicated. Statistics: t-test ***p<0.001 (n=3).

Figure 3A:
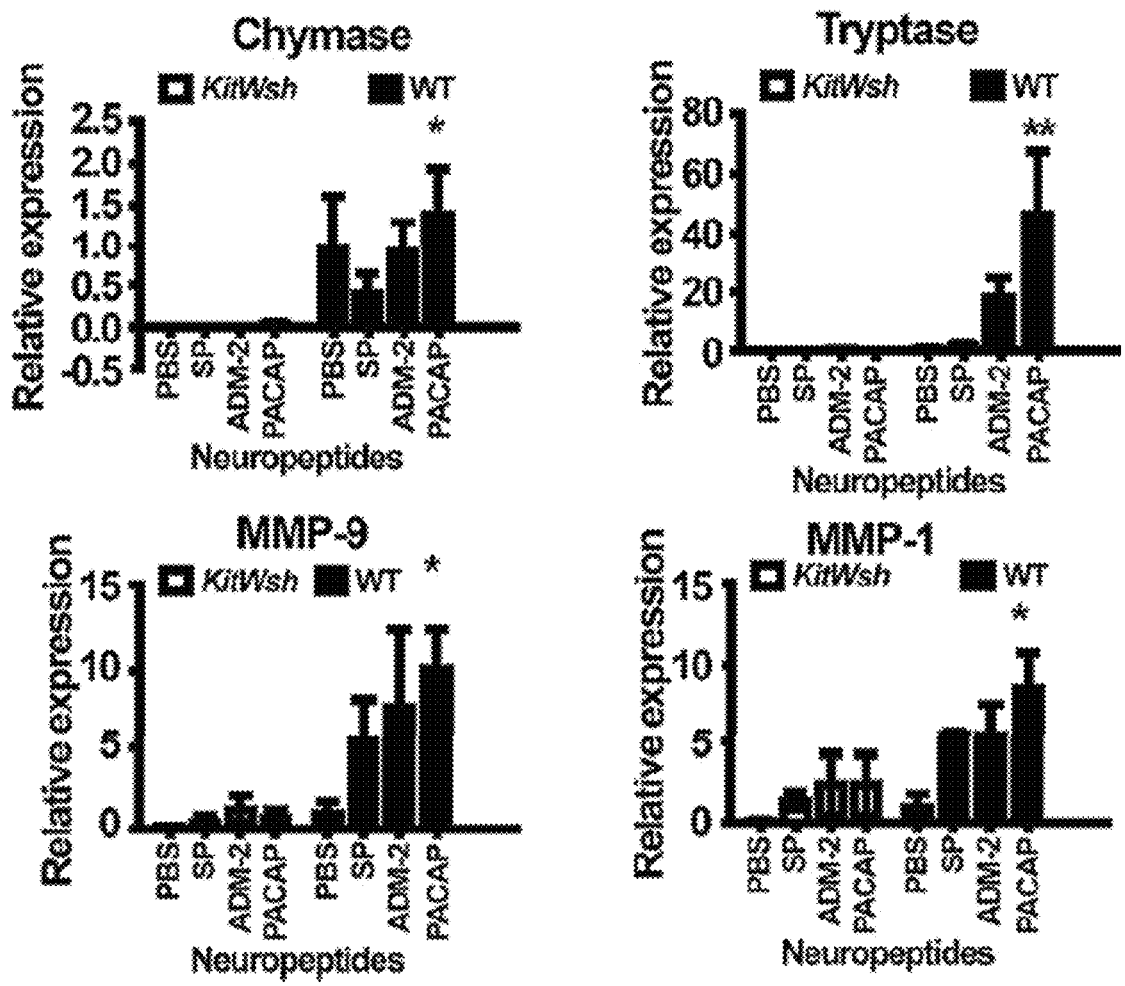
Figure 3B:
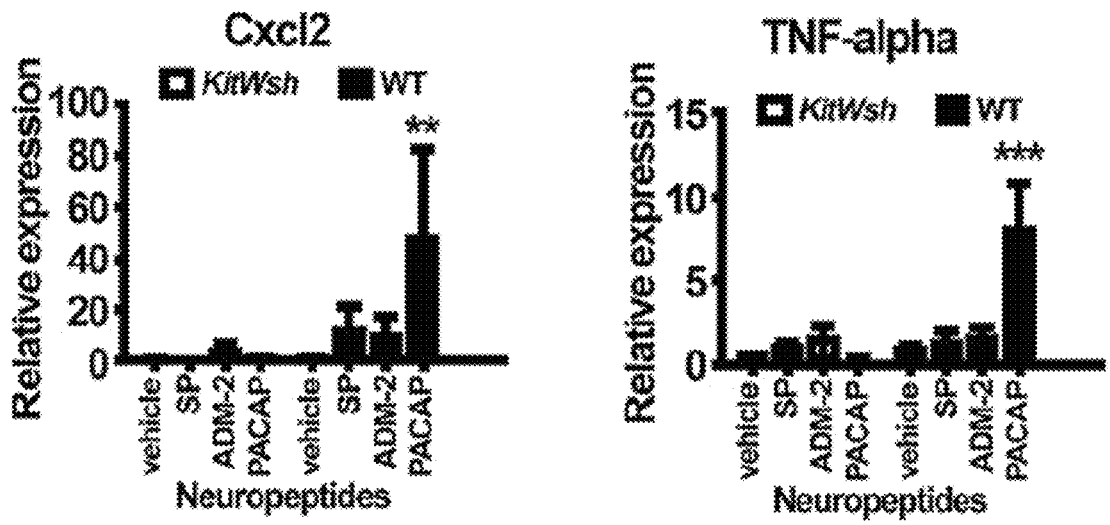

FIG. 3A-B shows neuropeptides induce the expression of inflammatory mediators in skin in a MC-dependent manner. WT and KitWsh$^{-/-}$ mice were injected with PBS or 100 μL of 1 μM neuropeptide (SP, substance P; ADM-2, adrenomedullin-2; PACAP, pituitary adenylate cyclase-activating peptide) intradermally, as indicated. Skin biopsies were harvested 6 hrs after injection and mRNA expressions of (a) proteases (chymase, tryptase, Mmp-9 and Mmp-1) and (b) proinflammatory cytokines (Cxcl2 and Tnf-α) were assessed by RT-PCR. Statistics: two-way ANOVA *p<0.05, p<0.01, *p<0.001 (n=3).

Figure 4A:
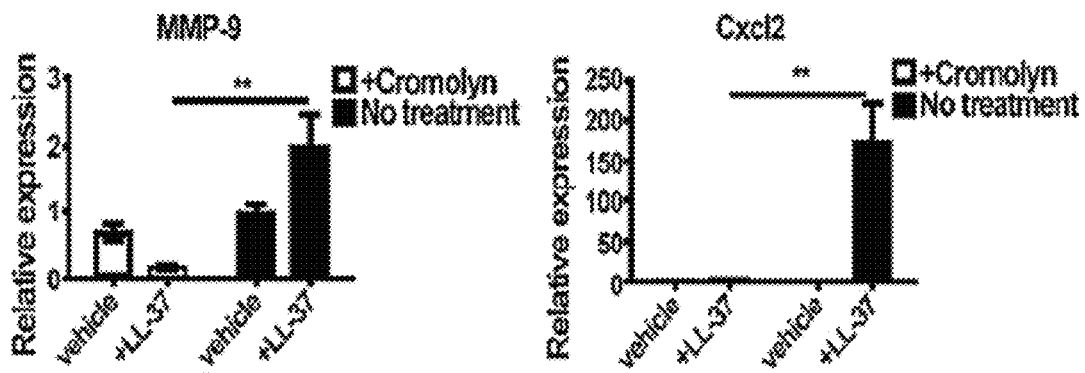
Figure 4B:
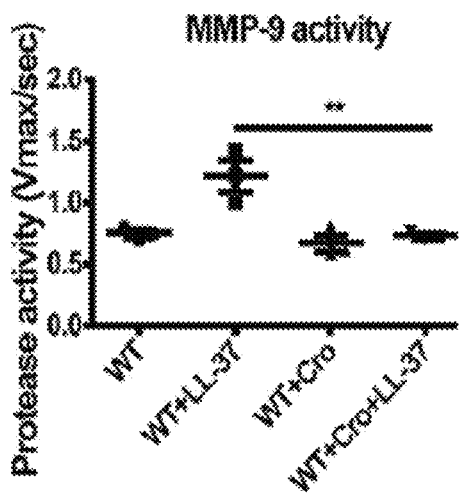
Figure 4C:
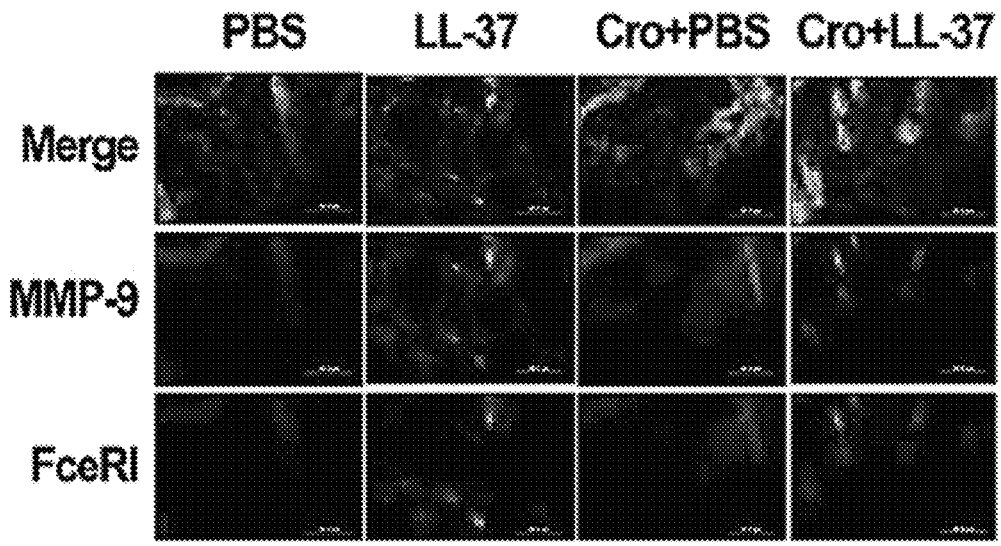

FIG. 4A-C shows treatment with the MC stabilizer, cromolyn, prevents mast cell (MC) degranulation. WT mice were injected I.P. with vehicle or cromolyn sodium (10 mg/kg, per day) for 4 days. 24 hours after the last injection, the mice were injected intradermally with 50 μl of 320 μm Cath LL-37 or PBS, twice a day for 2 days. Skin biopsies were taken after 72 hours of observation and (a) Mmp-9 and Cxcl2 mRNA expressions were assessed by RT-PCR, (b) MMP-9 activity was assessed by measuring cleavage of a MMP fluorogenic substrate with specific inhibitors, and (c) immunohistochemistry was performed on frozen skin sections using antibodies against MMP-9 and FcεRI. DAPI stain was also used, as indicated. Statistics: one-way and two-way ANOVA **p<0.01 (n=3).

Figure 5A:
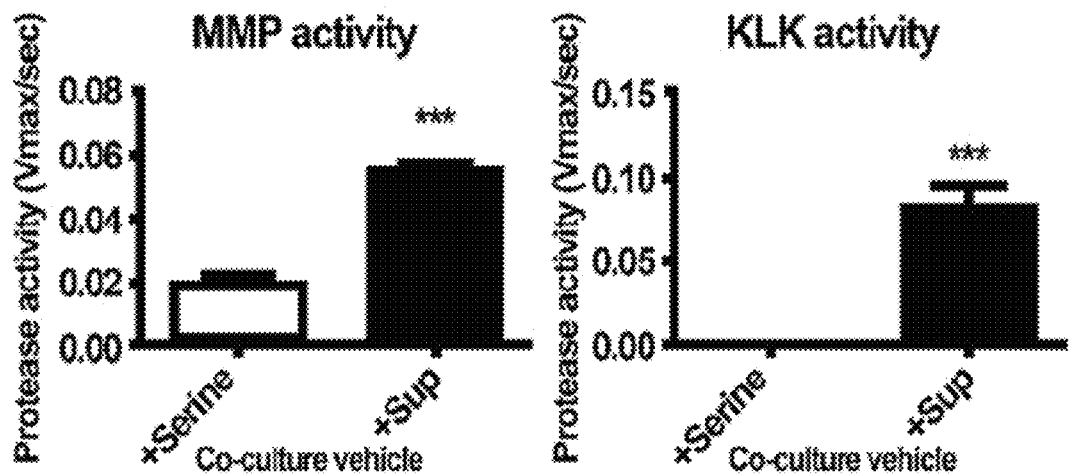
Figure 5B:
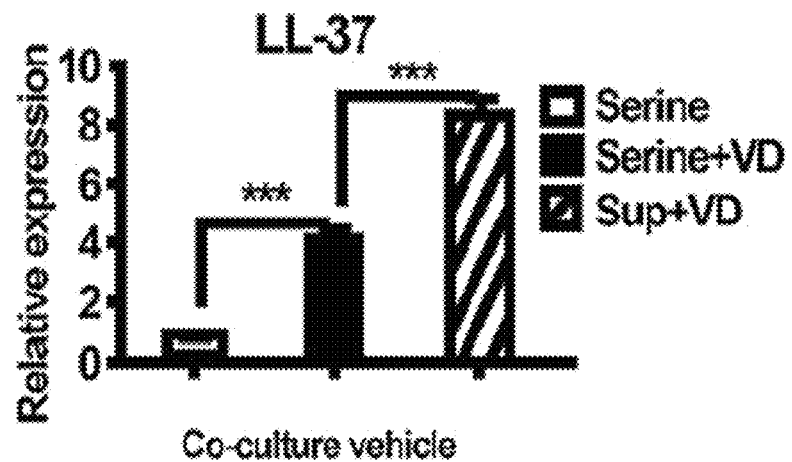
Figure 5C:
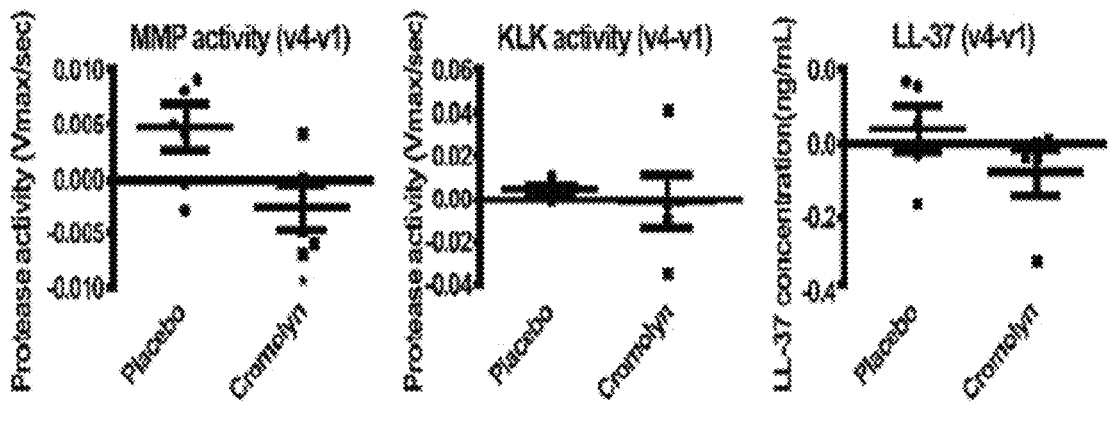

FIG. 5A-C shows MC proteases cause additional proteases production in *rosacea* skin. (a, b) NHEK cells were co-cultured with 100 μl of supernatant of human cord blood-derived MCs after degranulation by 48/80, or serine buffer. (a) After 24 hrs of co-culture, NHEK cells were washed well and MMP and KLK activities in the cells were obtained, and (b) For the comparison of Cath LL-37 mRNA expression in NHEK cells, 100 nM of 1,25(OH)$_2$VD3 was added to same co-culture. (c) 10 erythematotelangiectatic *rosacea* subjects were randomized to apply a solution containing either the MC stabilizer (4% cromolyn sodium) (n=5) or placebo (n=5) topically. Tape strips were obtained at the first visit (v1) and last visit (v4) and proteases and protein were separately extracted. Statistics: t-test ***p<0.001 (n=3), *p<0.05 (n=5).

Figure 6:
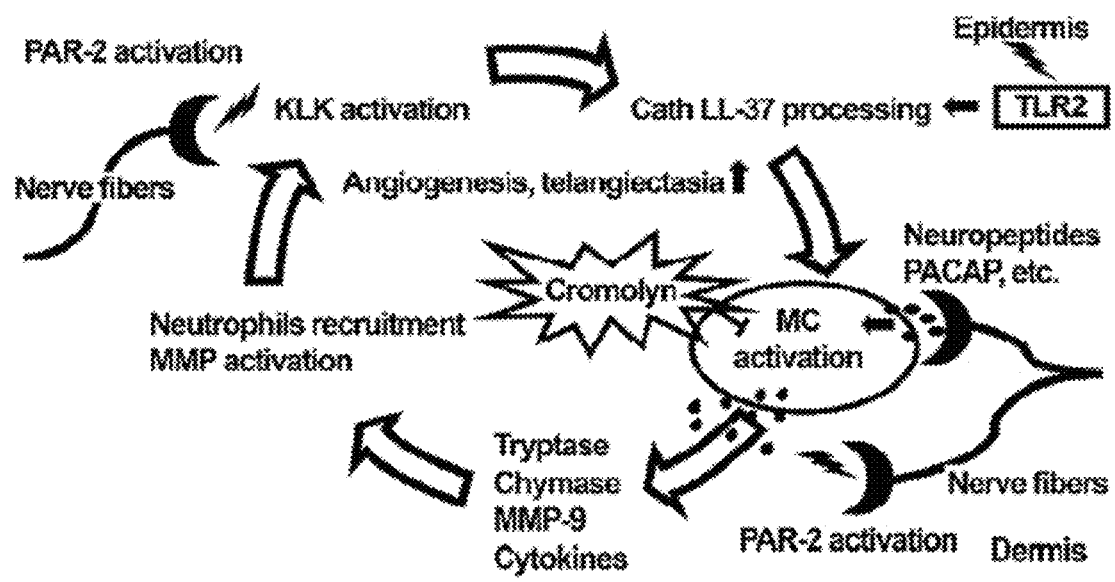

FIG. 6 shows a pathway leading to *rosacea* resulting from mast cell (MC) activation. *Rosacea* inflammation generated by altered production of cathelicidin in the epidermis is dependent on mast cell activation and its proteases that are released in the dermis. MC proteases, including MMP-9, may cause skin angiogenesis and telangiectasia that further promotes abnormal cathelicidin accumulation. Tryptic MC serine protease activates PAR-2 on sensory nerve endings in the dermis and released NPs activate MCs. A continuous inflammatory loop is amplified via mast cells, thus MC stabilizers (e.g., cromolyn) provide an effective therapeutic for *rosacea*.

DETAILED DESCRIPTION

As used herein and in the appended claims, the singular forms "a," "and," and "the" include plural referents unless the context clearly dictates otherwise. Thus, for example, reference to "a polynucleotide" includes a plurality of such polynucleotides and reference to "the polypeptide" includes reference to one or more polypeptides, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

*Rosacea* is a common facial dermatitis that currently affects an estimated 13 million Americans. It is a chronic and progressive cutaneous vascular disorder, primarily involving the malar and nasal areas of the face. *Rosacea* is characterized by flushing, erythema, papules, pustules, telanglectasia, facial edema, ocular lesions, and, in its most advanced and severe form, hyperplasia of tissue and sebaceous glands leading to rhinophyma. Rhinophyma, a florid overgrowth of the tip of the nose with hypervascularity and modularity, is an unusual progression of *rosacea* of unknown cause. Ocular lesions are common, including mild conjunctivitis, burning, and grittiness. Blepharitis, the most common ocular manifestation, is a nonulcerative condition of the lid margins.

Rosacea most commonly occurs between the ages of 30 to 60, and may be seen in women experiencing hormonal changes associated with menopause. Women are more frequently affected than men; the most severe cases, however, are seen in men. Fair complexioned individuals of Northern European descent are most likely to be at risk for rosacea; most appear to be pre-disposed to flushing and blushing. Although papules and pustules are associated with rosacea, and hence its misnomer as "acne rosacea", the occurrence of P. acnes is generally not associated with the condition.

The cause of rosacea is poorly understood, numerous theories have been offered. Hypotheses have included gastrointestinal, psychological, infectious, climatic, and immunological causes. A commonly proposed etiologic theory is based on the presence of Demodex folliculorum mites in patients with rosacea; the organism feeds on sebum, and in some cases treatment of Demodex infestation have provided improvement in the rosacea; however, in a review of biopsies, Demodex folliculorum was noted in only 19% of the specimens. A bacterial cause for the disease has been hypothesized, but no consistent findings of one bacteria have been demonstrated. Climate, specifically exposure to extremes of sun and cold, may have an effect on the course of the disease, but the role of climate is not clear. An autoimmune process has been suggested, and tissue fixed immunoglobulins have been reported in patients with chronic inflammation of rosacea, but no other evidence has been found. Other experimental evidence has suggested this disease may represent a type of hypersensitivity reaction. No single hypothesis appears to adequately explain both the vascular changes and the inflammatory reaction seen in rosacea, leaving the pathogenesis unclear.

Histopathologic findings in rosacea dermatitis include vascular dilatation of the small vessels with perivascular infiltration of histiocytes, lymphocytes, and plasma cells. Dermal changes include loss of integrity of the superficial dermal connective tissue with edema, disruption of collagen fibers, and frequently severe elastosis. Follicular localization is infrequent and, when seen, is usually manifest clinically as pustules. However, there is no primary follicular abnormality. Immunoglobulin and compliment deposition at the dermal-epidermal junction have been reported in conjunctival and skin biopsies from rosacea patients. Ocular pathologic findings include conjunctival and corneal infiltration with chronic inflammatory cells, including lymphocytes, epithelioid cells, plasma cells, and giant cells.

The disclosure demonstrates that individuals with rosacea express abnormally high levels of cathelicidin in their facial skin and that the proteolytically processed forms of cathelicidin peptides found in rosacea are increased and/or different from those present in normal individuals. These cathelicidin peptides are a result of a post-translational processing abnormality associated with an increase in stratum corneum tryptic enzyme (SCTE) in the epidermis. Experiments in which cathelicidin peptides were injected cutaneously into a subject in combination with an increased protease activity, by targeted deletion of the serine protease inhibitor gene Spink5 increased inflammation in mouse skin. The role of cathelicidin in enabling SCTE-mediated inflammation was verified in mice with a targeted deletion of Camp, the gene encoding cathelicidin. This data confirms the role of cathelicidin in skin inflammatory responses and provides an explanation for the pathogenesis of rosacea.

Recent discoveries have indicated that an alteration in the metabolism of LL-37 Cathelicidin (Cath LL-37) antimicrobial peptide, by KLKs and MMPs activity, is present in the human inflammatory process that leads to Rosacea. Although mast cells MCs contribute to overall host protection (Galli et al., 2008) by releasing a variety of molecules, including TNF-α (McLachlan et al., 2008), leukotriene B4 (Malaviya and Abraham, 2000), and cathelicidin AMP (Di Nardo et al., 2003), accumulated studies have also specifically implicated MCs in the development of inflammation in the skin (Kawakami et al., 2009; Lin et al., 2011; and Thurmond et al., 2008). Cathelicidin proteins are composed of two distinct domains: an N-terminal "cathelin-like" or "prosequence" domain and the C-terminal domain of the mature anti-microbial peptide (AMP). The C-terminal domain of cathelicidins was among the earliest mammalian AMPs to show potent, rapid, and broad-spectrum killing activity. The term "cathelin-like" derives from the similarity of the N-terminal sequence with that of cathelin, a 12 kDa protein isolated from porcine neutrophils that shares similarity with the cystatin superfamily of cysteine protease inhibitors.

Cathelicidins are expressed in neutrophils and myeloid bone marrow cells and most epithelial sources, and were the first AMPs discovered in mammalian skin due to their presence in wound fluid. In the neutrophil, cathelicidins are synthesized as full-length precursor and targeted to the secondary granules where they are stored. Upon stimulation, the full-length cathelicidin protein is proteolytically processed to unleash the microbialcidal activity of the C-terminal peptide from the cathelin-like domain. Human cathelicidin antimicrobial peptide (CAMP) gene is a direct target of the vitamin D receptor and is strongly up-regulated in myeloid cells by 1,25-dihydroxyvitamin D3 (see, e.g., FASEB Journal, 19:1067-1077, 2005).

The C-terminal 37 amino acids of human cathelicidin (LL-37) has been characterized. LL-37 was originally referred to as FALL39, named for the first 4 N-terminal amino acids of this domain and the total number of residues (i.e., 39). LL-37 is a peptide predicted to contain an amphipathic alpha helix and lacks cysteine, making it different from all other previously isolated human peptide antibiotics of the defensin family, each of which contain 3 disulfide bridges. Full length human cathelicidin (sometimes referred to as full length LL-37) comprises the cathelin-like precursor protein and the C-terminal LL-37 peptide, thus comprising 170 amino acids (SEQ ID NO:2).

The polypeptide comprising SEQ ID NO:2 has a number of distinct domains. For example, a signal domain comprising a sequence as set forth from about 1 to about 29-31 of SEQ ID NO:2 is present. The signal domain is typically cleaved following amino acid number 30 of SEQ ID NO:2, however, one of skill in the art will recognize that depending upon the enzyme used, the expression system used and/or the conditions under which proteolytic cleavage of the polypeptide takes place, the cleavage site may vary from 1 to 3 amino acid in either direction of amino acid number 30 of SEQ ID NO:2. Another domain comprises the N-terminal domain, referred to as the cathelin-like domain. The cathelin-like domain comprises from about amino acid 29 (e.g., 29-31) to about amino acid 128 (e.g., 128-131) of SEQ ID NO:2. Yet another domain of SEQ ID NO:2 comprises the C-terminal domain referred to as LL-37. The LL-37 domain comprises from about amino acid 128 (e.g., 128-134) to amino acid 170 of SEQ ID NO:2. The full length LL-37 polypeptide is set forth in SEQ ID NO:2.

The human cDNA sequence for full length LL-32 is set forth in SEQ ID NO:1. The coding sequence of an active fragment of LL-37 can be identified with reference to the cDNA sequence provided in SEQ ID NO:1 without difficulty. Accordingly the corresponding coding sequences of the fragments identified herein are also provided by the disclosure. The development of antisense and ribozyme molecules useful in the methods and compositions of the invention can be readily identified based upon the sequence listing provided herein as well as reference to variants and homologs known in the art.

As used herein, the term "skin" refers to the outer protective covering of the body of a mammal (e.g., a human), consisting of the corium and the epidermis, and is understood to include sweat and sebaceous glands, as well as hair follicle structures. Throughout the disclosure, the adjective "cutaneous" can be used, and should be understood to refer generally to attributes of the skin, as appropriate to the context in which they are used.

Mast cells (MCs) are one of the primary sources of Cath LL-37 and proteases in the skin and are increased within the skin of *Rosacea* patients. MC proteases are not only able to recruit other immune cells and amplify the inflammation, but also cause vasodilation and angiogenesis; moreover, MCs play an important role in mediating signals between the sensory nerve ending and the dermis.

In addition to inflammation, neuronal dysregulation is equally important to *rosacea* pathogenesis. In fact, neuronal dysregulation contributes to the disease via various mechanisms, such as vasomotor instability, release of pro-inflammatory neuropeptides, and neuronal injury (Wang et al., 2008; and Roosterman et al., 2006). MCs can also be activated by neuropeptides to release their components upon cell degranulation. Neuropeptides have also been shown to induce the production of TNF-α, CCL2, CCL5, CXCL9, CXCL10, and CXCL8 in human mast cells (Kulka et al., 2008), which leads to the recruitment of dendritic cells/ macrophages (via CCL2), TH1 lymphocytes (via CCL5, CXCL9, or CXCL10) and neutrophils (via CXCL8) (Gangavarapu et al., 2012). As described below, the disclosure demonstrates that neuropeptides induce MC enzyme activation and subsequent Cath LL-37 generation from hCAP18. Further, the data shows that MCs are mediators of the stress-response network in skin inflammation (Arck et al., 2006). Thus, the disclosure demonstrates that MCs and MC proteases affect the development of skin inflammation in *rosacea* and provide the in vivo interconnections between MCs, epidermal keratinocytes and sensory nerves.

Vitamin D3 leads to increased expression of Toll-like receptor 2 (TLR2) and CD14, which in turn induce antimicrobial peptides. Thus, Vitamin D3 both induces cathelicidin and enables TLR2 responsiveness to further increase expression of cathelicidin. For example, normal keratinocytes stimulated with Vitamin D3 show induced the expression of cathelicidin in normal human keratinocytes as well as the keratinocytic cell line HaCat. A vitamin D3 response element in the cathelicidin promoter was necessary for cathelicidin production. In particular, 1,25 OH D3 induces the expression of LL-37.

Vitamin D3 is produced from dietary or endogenous precursors under the influence of UVB light. Activation of vitamin D3 to 1,25 OH D3 requires two major hydroxylation steps, the first by 25-hydroxylase (CYP27A1) and then by 1α-hydroxylase (CYP27B1). These enzymes are mainly located in the human liver and kidney, respectively. However, some 1,25 OH D3 targeted organs such as the epidermis also possess the enzymes to produce 1,25 OH D3. Upon binding to the vitamin D receptor (VDR), 1,25 OH D3 activates target genes through vitamin D responsive elements in the gene promoter. Simultaneously, 1,25 OH D3 induces the vitamin D3 catabolic enzyme CYP24A1 (24-hydroxylase) thereby initializing its own degradation. Control of 1,25D3 producing and catabolizing enzymes therefore determines the level of bioactive hormone.

1,25 OH D3 hydroxylase, and specific receptors in several tissues, capable of converting non-active vitamin D3 to active 1,25 OH D3 are found in such tissues as bone, keratinocytes, placenta, and immune cells. Accordingly, inhibiting the activity of such enzymes may prove useful for treating inflammatory diseases and disorders of the epithelium (e.g., *rosacea*, *acnes* and the like). Furthermore, increased catabolic activity that degrades active vitamin D3 can be used to treat such diseases and disorders (e.g., *rosacea*). For example, stimulating the vitamin D3 catabolic enzyme CYP24A1 can reduce the amount of vitamin D3 present in the skin and thereby reduce the stimulatory effect vitamin D3 has on cathelicidin production.

The disclosure is based, in part, upon abnormal proteolytic processing as an etiologic explanation for *rosacea* and provides a therapeutic approach to this disorder. Skin of subjects with *rosacea* express more cathelicidin than normal facial skin. Additionally, levels of the cathelicidin precursor protein hCAP18, cathelicidin peptides LL-37 and FA-29, and the serine protease kallikrein (SCTE) are significantly higher in *rosacea* skin than in normal skin. The disclosure provides compositions and methods to reduce the proteolytic processing of the LL-37 precursor protein and thus reducing the amount of activated LL-37.

The disclosure also demonstrate that mast cell stabilizers can inhibit the progression or development of skin inflammation and *rosacea*. Thus, the disclosure provides methods and compositions for the treatment of cutaneous inflammatory diseases and disorders. The disclosure provides methods and compositions useful for the treatment of inflammatory diseases and disorders of the skin including, but not limited to, *rosacea* and *acnes*. For example, a drug that targets and inhibits cathelicidin proteolysis or reduction in cathelicidin production or activity provides an effective treatment of *rosacea*. One can treat *rosacea* by inhibiting cathelicidin expression through topical inhibition of Vitamin D or the Vitamin D receptor to reduce up regulation of cathelicidin, or inhibit the kallikrein stratum corneum tryptic enzyme (SCTE), an enzyme that cleaves the cathelicidin precursor protein, with serine protease inhibitors or by inhibiting neuropeptide activation of Mast cells or by using a mast cell stabilizer (see, e.g., FIG. 6). Combinations of any of the foregoing can also be used.

The disclosure is based upon the experiments summarized below in the Examples section which indicate that mast cell stabilizers can be used to treat *rosacea* by inhibiting mast cell activation and/or cathelicidin processing. The mast cell stabilizer can be used alone or in combination with other agents that inhibit cathelicidin processing (e.g., Vitamin D3, protease inhibitors and the like).

In one aspect of the disclosure, a method of treatment of inflammatory diseases and disorders, *rosacea* and or *acnes* comprises inhibiting mast cell activation comprising contacting a mast cell in the skin of a subject with a mast cell stabilizer. In one embodiment, the mast cell stabilizer is selected from the group consisting of lodoxamide tromethamine, nedocromil sodium, cromolyn sodium, and pemirolast potassium. In a further embodiment, the method may be combined with the administration of a vitamin D3 antagonist, a serine protease inhibitor and/or an agent that inhibits cathelicidin expression or activity. Examples of compositions and methods for inhibiting the expression of cathelicidins include using mast cell antisense, ribozyme and gene therapy techniques. For example, *rosacea* can be inhibited or treated using a mast cell stabilizer in combination with an antisense or ribozyme therapies that reduce the expression of cathelicidin. In another embodiment, a vitamin D inhibitor, or vitamin D receptor antagonist can be used to reduce expression of a cathelicidin. Examples of compositions and methods for inhibiting cathelicidin activity include antibodies and small molecule agents. In another embodiment, the treatment is at the site of inflammation through topical inhibition of vitamin D activity, inhibiting of a vitamin D receptor activity, or an inhibitor of a protease that cleaves full length cathelicidin, or an inhibitor of production of such proteases by, for example, mast cells. Serine protease inhibitors such as aprotinin and 4-(2-aminoethyl)-benzenesulfonylfluoride (AEBSF) can inhibit this enzyme in vitro.

A inflammatory inhibitory composition (e.g., a *rosacea* inhibitory composition) of the disclosure used in the treatment of *rosacea* comprises (i) a mast cell stabilizer, (ii) a neuropeptide inhibitor (e.g., an antibody thereto), (iii) a cathelicidin activity or expression inhibitor, (iv) a serine protease activity or expression inhibitor (e.g., a SCTE inhibitor), or (v) a combination of (i-iv).

In one embodiment, the disclosure provides a method for treating or preventing *rosacea* in either an animal or human by administering an effective amount of a drug that stabilizes mast cells either alone or in combination with secondary active agents. The term "effective amount" refers to a sufficient quantity of drug to achieve a therapeutic objective. In the present case, this means that a sufficient amount of mast cell stabilizer is administered to inhibit the *rosacea* and/or the production of and processing of cathelicidin.

The mast cell stabilizing drug that is administered in the method described above will typically be divided into two or more equal doses given over a 24 hour period. Examples of mast cell stabilizing drugs include, but are not limited to, lodoxamide tromethamine, nedocromil, cromolyn, ketotifen and pemirolast potassium. These may be given in any pharmaceutically acceptable form, including pharmaceutically acceptable salts, such as sodium, disodium, potassium or lithium salts. It will be understood that, unless otherwise indicated, reference to one of these drugs includes all of its pharmaceutically acceptable forms. Some typical forms are: nedocromil sodium (especially at 5-50 mg per day when delivered topically or 50-500 mg per day when delivered orally); ketotifen fumarate (when delivered orally at 1-200 mg per day) and lodoxamide tromethamine (when delivered orally at 1-200 mg per day). The most common mast cell stabilizing drug is cromolyn sodium or disodium, administered orally at a dosage of 200-1,000 mg per day.

All dosages mentioned herein are with respect to the administration of drugs to humans. If the drugs are administered to an animal, the dosage for humans may be used to provide guidance and an adjustment made for difference in weight. For example, an animal weighing about 50 lbs would receive about one third of the dose of a human.

The method described above may be performed to either to inhibit the progression or severity of symptoms of *rosacea* in an individual diagnosed with *rosacea* or prevent the onset of *rosacea* in individual suspect of having or having *rosacea*. When given to a human or animal to treat *rosacea*, drug administration should be continued on a daily basis until the symptoms of *rosacea* have subsided. In one embodiment, individuals will be administered cromolyn, particularly cromolyn sodium or disodium, at a dose of about 200-1,000 mg daily for this duration.

In another embodiment, the disclosure is directed to a therapeutic composition having both a mast cell stabilizer and an inhibitor of cathelicidin processing (e.g., a protease inhibitor). The stabilizer should be part of a pharmaceutical composition in unit dose form and be packaged in a finished pharmaceutical container. The term "unit dose form" refers to a single drug administration entity, such as a tablet, capsule, topical formulation (e.g., spray or lotion) or quantity of solution. A "finished pharmaceutical container" refers to any of the different types of packaging typically used for pharmaceuticals such as bottles, vials, blister packs, etc. For the purposes of the disclosure, a finished pharmaceutical container will include packaging designed for the oral or topical administration of drugs, i.e., bottles or vials that contain, and can be used to deliver, a solution or powder as a spray. Similarly, a "unit dose form" will include a solution in which drug is dissolved at a concentration that provides a therapeutic effect when administered to a patient topically or orally in a fixed amount.

Drugs that stabilize mast cells have been studied extensively in connection with the treatment of allergies and several of these drugs are available commercially. The most common mast cell stabilizers are cromolyn, nedocromil, ketotifen and lodoxamide and may either be purchased or synthesized using methods well known in the art. In addition, any of the other pharmaceutically acceptable mast cell inhibitors described in the art may be used in various embodiments described herein. These include compounds disclosed in U.S. Pat. Nos. 6,207,684; 4,634,699; 6,207,684; 4,871,865; 4,923,892; 6,225,327; and 7,060,827 (the disclosure of which are incorporated herein by reference). Methods for preparing the compounds are presented in each of the U.S. patents along with information on how the compounds may be purified and the forms in which they may be used. These compounds may be given to patients in any pharmaceutically acceptable form, including any pharmaceutically acceptable salt, with the typical drug being either sodium or disodium cromolyn.

There are a number of commercially and clinically relevant serine protease inhibitors that can be used in the methods and compositions of the disclosure in combination with or administered simultaneously with a mast cell stabilizer. Thus, a composition and method useful for treatment of skin inflammation such as *rosacea* can include a mast cell stabilizer and further comprise any number of serine protease inhibitors such as those disclosed in, for example, U.S. Pat. Nos. 5,786,328, 5,770,568, or U.S. Pat. No. 5,464,820, which states in part: One embodiment of the invention is directed to substrate analogs of tissue kallikrein. These substrate analogs comprise a peptide with an amino acid sequence corresponding to positions 388 to 390 of tissue kallikrein. Peptides may be made synthetically, genetically by recombinant engineering techniques, such as by cloning and expressing of a nucleic acid sequence, or purified from natural sources such as a bacterial, fungal or cellular extracts. The structure, chemical, physicochemical, nomenclature and analytical aspects of amino acids are described in Chemistry of the Amino Acids (J. P. Greenstein and M. Winitz editors, John Wiley & Sons, New York, N.Y., 1961, reprinted 1984), which is hereby specifically incorporated by reference. The peptides are comprised of modified and/or unmodified amino acids which include the naturally occurring amino acids, the non-naturally occurring (non-coding) amino acids, synthetically made amino acids, and combinations thereof. The naturally occurring amino acids include glycine (Gly), the amino acids with alkyl side chains such as alanine (Ala), valine (Val), leucine (Leu), isoleucine (Ile), and proline (Pro), the aromatic amino acids phenylalanine (Phe), tyrosine (Tyr) and tryptophan (Trp), the amino acid alcohols serine (Ser) and threonine (Thr), the acidic amino acids aspartic acid (Asp) and glutamic acid (Glu), the amides of Asp and Glu, asparagine (Asn) and glutamine (Gln), the sulfur-containing amino acids cysteine (Cys) and methionine (Met), and the basic amino acids histidine (His), lysine (Lys), and arginine (Arg). The non-naturally occurring amino acids include, for example, ornithine (Orn), norleucine (Nle), citralline (Cit), homo-citralline (hCit), desmosine (Des), and isodesmosine (Ide). Modified amino acids include derivatives and analogs of naturally and non-naturally occurring, and synthetically produced amino acids. Such amino acid forms have been chemically modified such as, for example, by halogenation of one or more active sites with chlorine (Cl), bromine (Br), fluorine (F), or iodine (I), alkylation with a carbon containing group such as a methyl (Me), ethyl (Et), butyl (Bu), amino (NH2 or NH3), amidino (Am), acetomidomethyl (Acm), or phenyl (Ph) group, or by the addition of a phosphorous (P), nitrogen (N), oxygen (O) or sulfur (S) containing group. Modifications may also be made by, for example, hydration, oxidation, hydrogenation, esterification, or cyclization of another amino acid or peptide, or of a precursor chemical. Examples include the amino acid hydroxamates and decarboxylases, the dansyl amino acids, the polyamino acids, and amino acid derivatives. Specific examples include gamma amino butyric acid (GABA), hydroxyproline (Hyp), aminoadipic acid (Aad) which may be modified at the 2 or 3 position, o-aminobutyric acid (Aab or Abu), selenocysteine (SeCys2), tert-butylglycine (Bug or tert-BuGly), the N-carbamyl amino acids, the amino acid methyl esters, amino-propionic acid (or β-alanine; 13-Ala), adamentylglycine (Adg), aminocaproic acid (Acp), N-ethylasparagine (Et-Asn), allo-hydroxylysine (aHyl), allo-isoleucine (aIle), phenylglycine (Phg), pyridylalanine (Pal), thienylalanine (Thi), α-Δ-aminobutyric acid (Kbu), α-β-diaminopropionic acid (Kpr), 1- or 2-naptithylalanine (1Nal or 2Nal), orthofluorophenylalanine (Phe (o-F)), N-methylglycine (MeGly), N-methyl-isoleucine (MeIle), N-methyl-valine (MeVal), 2-amino-heptanoic acid (Ahe), 2- or 3-amino-isobutyric acid (Aib), 2-amino-pimellic acid (Dbu), 2-2'-diaminopimellic acid (Dpm), 2,3-diaminopropionic acid (Dpr), and N-ethylglycine (EtGly). Chemically produced non-coded amino acids include, for example, phenylglycine (Ph-Gly), cyclohexylalanine (Cha), cyclohexylglycine (Chg), and 4-amino phenylalanine (Phe (4NH2) or Aph). Modified amino acids may also be chemical structures which are not amino acids at all, but are actually classified as another chemical form such as an alkyl amine, a saccharide, a nucleic acid, a lipid, a fatty acid or another acid. Any of the modified or unmodified amino acids which comprise the peptide may be in the D- or L-conformations or comprise one, two or more tautomeric or resonance forms. All amino acids disclosed herein are in the L-conformation unless otherwise indicated the disclosures of which are incorporated herein by reference.

A vitamin D receptor inhibitor includes antagonistic vitamin D analogs, small molecules, and soluble vitamin D receptor polypeptides. For example, a class of vitamin D analogs referred to as 19-nor vitamin D analogs, which are characterized by the replacement of the A-ring exocyclic methylene group (carbon 19), typical of the vitamin D system, by two hydrogen atoms are useful for generating receptor antagonists. Further substitution at the 2-position and/or modification of the side chain attached to carbon 17 of the five-membered ring has led to pharmacologically active compounds at physiologically active concentrations compared to the native hormone. Related compounds having a 2α-methyl group have also been disclosed (Fujishima et al., Bioorg. Med. Chem. 11, 3621-3631, 2003). Select analogs exhibit antagonistic activity with respect to the vitamin D receptor and are effective for use in treating rosacea. Various methods of synthesizing 19-nor-vitamin D analogs have been disclosed (see, e.g., Perlman et al., Tetrahedron Lett. 31, 1823 (1990); Perlman et al., Tetrahedron Lett. 32, 7663 25 (1991), and DeLuca et al., U.S. Pat. No. 5,086,191). The synthesis of intermediates for use in the preparation of various 19-nor vitamin D analogs is disclosed in U.S. Pat. No. 5,086,191, which is incorporated by reference herein. Another antagonist includes 6-fluoro-vitamin D3 (6-F-D3). The disclosure provides methods for antagonizing the vitamin D receptor, methods for treating conditions such as rosacea, and the use of various vitamin D analogs in preparing medicaments for use in antagonizing the vitamin D receptor and/or treating conditions such as rosacea.

A cathelicidin activity inhibitor includes any agent that reduces the biological activity of a cathelicidin polypeptide (e.g., an N-terminal or C-terminal domain of cathelicidin). Exemplary cathelicidin inhibitory agents include antibodies that bind to and inhibit (a) a cathelicidin polypeptide, (b) a functional fragment of cathelicidin, (c) enzymes that cleave cathelicidin to an activated form. Further cathelicidin inhibitory agents include enzymes that degrade cathelicidin polypeptide to inactive peptides and the like. A cathelicidin expression inhibitor includes, for example, antisense molecules, ribozymes and small molecule agents (e.g., vitamin D3 antagonists) that reduce the transcription or translation of a cathelicidin polynucleotide (e.g., DNA or RNA). A serine protease activity inhibitor includes any agent that reduces the biological activity of a serine protease polypeptide (e.g., a SCTE polypeptide). Exemplary serine protease inhibitory agents include antibodies that bind to and inhibit a serine protease polypeptide or functional fragment thereof, enzymes that degrade a serine protease polypeptide to inactive peptides, and the like. A serine protease expression inhibitor includes, for example, antisense molecules, ribozymes and small molecule agents (e.g., vitamin D antagonists) that reduce the transcription or translation of a serine protease polynucleotide (e.g., DNA or RNA).

As described herein, mast cells produce a number of the proteases that act upon the pro-form of cathelicidin to generate LL-37. Accordingly, molecules that inhibit mast cell activation including mast cell stabilizers and antagonists of neuropeptides will down regulate the production of matrix metalloproteinase and other protease that act on cathelicidin and on the skin tissue thereby reducing LL-37 and inhibiting rosacea.

The disclosure provides therapeutic compositions comprising mast cell stabilizers selected from the group consisting of cromolyn, nedocromil, ketotifen and lodoxamide. In one embodiment, the therapeutic compositions is formulated for topical administration. In this embodiment, the topical formulation can be a lotion, spray or ointment. In another embodiment, the therapeutic composition can be formulated for oral delivery. When these drugs are given orally in the form of a tablet or capsule, a unit dose will typically be between 5 and 1,000 mg and more typically between 10 and 500 mg. An equivalent amount would be in a unit dose form administered as an oral solution. If the drugs are given nasally, then solutions should typically contain a sufficient concentration of drug so that a patient receives between 0.1 and 10 mg per spray.

Mast cell stabilizing drugs may be incorporated into pharmaceutical compositions in accordance with methods that are standard in the art (see e.g., Remington's Pharmaceutical Sciences, Mack Publishing Co., (1990)). Formulations may be designed for delivery by any of the routes commonly used in the art, with preparations designed for oral or topical delivery being useful for treating *rosacea*. For oral compositions, e.g. tablets or capsules, the mast cell stabilizing drug should typically be present in an amount of between 1 and 500 mg. In compositions for topical delivery, stabilizers will typically be present at about 0.5 mg/ml to about 50 mg/ml and more commonly at about 1 mg/ml to about 20 mg/ml.

Mast cell stabilizers may be used in conjunction with any of the vehicles and excipients commonly employed in pharmaceutical preparations including water, salt solutions, alcohols, gum arabic, vegetable oils, benzo-alcohols, polyethylene glycol, gelatin, carbohydrates such as lactose, amylase, or starch; magnesium stearate; talc; salycic acid; paraffin; fatty acid esters; polymers; and the like. The pharmaceutical preparations can be sterilized and, if desired, mixed with auxiliary agents such as: dispersants; lubricants; preservatives; stabilizers; wetting agents; emulsifiers; salts for influencing osmotic pressure; buffers; coloring agents; flavoring agents; and/or aromatic substances.

Solutions, particularly solutions for injection, can be prepared using water or physiologically compatible organic solvents such ethanol, 1,2-propylene glycol; polygycols; dimethylsulfoxides; fatty alcohols; triglycerides; partial esters of glycerine; and the like. The preparations can be made using conventional techniques and may include sterile isotonic saline, water, 1,3-butanediol, ethanol, 1,2-propylene glycol, polygycols mixed with water, ringers Ringer's solution etc.

The methods of treating *rosacea* using a mast cell stabilizer is compatible with any route of administration including oral, perioral, topical, internal, rectal, nasal, lingual, transdermal, vaginal, intravenous, intra-arterial, intramuscular, intraperitoneal, intracutaneous and subtaneous routes. Dosage forms that may be used include tablets, capsules, powders, aerosols, ointments, lotions, suppositories, skin patches, parenterals, sustained release preparations and oral liquids, including suspensions solutions and emulsions. Typically the compositions are delivered orally or topically. If desired, compositions, particularly compositions for injection, may be freeze-dried and lyophilizates reconstituted before administration. Dosage forms may include mast cell stabilizers as the sole active ingredient or they may include other active agents as well. All dosage forms may be prepared using methods that are standard in the art and that are taught in reference works such as Remington's Pharmaceutical Sciences (Osol, A, ed., Mack Publishing Co. (1990)).

In one aspect, an inflammatory/*rosacea* inhibitory composition of the disclosure may be formulated for topical administration (e.g., as a lotion, cream, spray, gel, or ointment). Such topical formulations are useful in treating or inhibiting *rosacea* at the site of the disorder. Examples of formulations in the market place include topical lotions, creams, soaps, wipes, and the like. It may be formulated into liposomes to reduce toxicity or increase bioavailability. Other methods for delivery of the composition include oral methods that entail encapsulation of the cathelicidin inhibitor in microspheres or proteinoids, aerosol delivery (e.g., to the lungs), or transdermal delivery (e.g., by iontophoresis or transdermal electroporation) and eye drops. Other methods of administration will be known to those skilled in the art.

Preparations for parenteral administration of an inflammatory/*rosacea* inhibitory composition of the disclosure include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, anti-oxidants, cheating agents, inert gases and the like also can be included.

Typically an inflammatory/*rosacea* inhibitory composition of the disclosure will comprise a pharmaceutically acceptable carrier and may comprise one or more additional agents useful for delivery to a subject. An inflammatory/*rosacea* inhibitory composition will typically be formulated for topical application to a site of inflammatory or *rosacea*.

A pharmaceutical or cosmetic composition of the disclosure comprises, for example, an inflammatory/*rosacea* inhibitory composition and one or more additional agents. The one or more additional agents can include a pharmaceutically acceptable carrier alone or in combination with a skin lightening agent, a sunscreen agent, a skin conditioning agent, a skin protectant, an emollient, a humectant, or a mixture thereof. Various formulations for topical delivery are known in the art.

Suitable skin lightening agents include, but are not limited to, ascorbic acid and derivatives thereof; kojic acid and derivatives thereof; hydroquinone; azelaic acid; and various plant extracts, such as those from licorice, grape seed, and bear berry. A skin conditioning agent includes, for example, a substance that enhances the appearance of dry or damaged skin, as well as a material that adheres to the skin to reduce flaking, restore suppleness, and generally improve the appearance of skin. Representative examples of a skin conditioning agent that may be used include: acetyl cysteine, N-acetyl dihydrosphingosine, acrylates/behenyl acrylate/dimethicone acrylate copolymer, adenosine, adenosine cyclic phosphate, adenosine phosphate, adenosine triphosphate, alanine, albumen, algae extract, allantoin and derivatives, aloe barbadensis extracts, amyloglucosidase, arbutin, arginine, bromelain, buttermilk powder, butylene glycol, calcium gluconate, carbocysteine, carnosine, beta-carotene, casein, catalase, cephalins, ceramides, chamomilla recutita (matricaria) flower extract, cholecalciferol, cholesteryl esters, coco-betaine, corn starch modified, crystallins, cycloethoxymethicone, cysteine DNA, cytochrome C, darutoside, dextran sulfate, dimethicone copolyols, dimethylsilanol hyaluronate, elastin, elastin amino acids, ergocalciferol, ergosterol, fibronectin, folic acid, gelatin, gliadin, beta-glucan, glucose, glycine, glycogen, glycolipids, glycoproteins, glycosaminoglycans, glycosphingolipids, horseradish peroxidase, hydrogenated proteins, hydrolyzed proteins, jojoba oil, keratin, keratin amino acids, and kinetin. Other non-limiting examples of a skin conditioning agent that may be included in the compositions includes lactoferrin, lanosterol, lecithin, linoleic acid, linolenic acid, lipase, lysine, lysozyme, malt extract, maltodextrin, melanin, methionine, niacin, niacinamide, oat amino acids, oryzanol, palmitoyl hydrolyzed proteins, pancreatin, papain, polyethylene glycol, pepsin, phospholipids, phytosterols, placental enzymes, placental lipids, pyridoxal 5-phosphate, quercetin, resorcinol acetate, riboflavin, *Saccharomyces* lysate extract, silk amino acids, sphingolipids, stearamidopropyl betaine, stearyl palmitate, tocopherol, tocopheryl acetate, tocopheryl linoleate, ubiquinone, *Vitis vinifera* (grape) seed oil, wheat amino acids, xanthan gum, and zinc gluconate. Skin protectant agents include, for example, a compound that protects injured or exposed skin or mucous membrane surfaces from harmful or irritating external compounds. Representative examples include algae extract, allantoin, aluminum hydroxide, aluminum sulfate, *Camellia sinensis* leaf extract, cerebrosides, dimethicone, glucuronolactone, glycerin, kaolin, lanolin, malt extract, mineral oil, petrolatum, potassium gluconate, and talc.

An emollient may be included in a pharmaceutical or cosmetic composition of the disclosure. An emollient generally refers to a cosmetic ingredient that can help skin maintain a soft, smooth, and pliable appearance. Emollients typically remain on the skin surface, or in the stratum corneum, to act as a lubricant and reduce flaking. Some examples of an emollient include acetyl arginine, acetylated lanolin, algae extract, apricot kernel oil polyethylene glycol-6 esters, avocado oil polyethylene glycol-11 esters, bis-polyethylene glycol-4 dimethicone, butoxyethyl stearate, glycol esters, alkyl lactates, caprylyl glycol, cetyl esters, cetyl laurate, coconut oil polyethylene glycol-10 esters, alkyl tartrates, diethyl sebacate, dihydrocholesteryl butyrate, dimethiconol, dimyristyl tartrate, distearath-5 lauroyl glutamate, ethyl avocadate, ethylhexyl myristate, glyceryl isostearates, glyceryl oleate, hexyldecyl stearate, hexyl isostearate, hydrogenated palm glycerides, hydrogenated soy glycerides, hydrogenated tallow glycerides, isostearyl neopentanoate, isostearyl palmitate, isotridecyl isononanoate, laureth-2 acetate, lauryl polyglyceryl-6 cetearyl glycol ether, methyl gluceth-20 benzoate, mineral oil, myreth-3 palmitate, octyldecanol, octyldodecanol, *odontella aurita* oil, 2-oleamido-1,3 octadecanediol, palm glycerides, polyethylene glycol avocado glycerides, polyethylene glycol castor oil, polyethylene glycol-22/dodecyl glycol copolymer, polyethylene glycol shea butter glycerides, phytol, raffinose, stearyl citrate, sunflower seed oil glycerides, and tocopheryl glucoside.

Humectants are cosmetic ingredients that help maintain moisture levels in skin. Examples of humectants include acetyl arginine, algae extract, aloe barbadensis leaf extract, 2,3-butanediol, chitosan lauroyl glycinate, diglycereth-7 malate, diglycerin, diglycol guanidine succinate, erythritol, fructose, glucose, glycerin, honey, hydrolyzed wheat protein/polyethylene glycol-20 acetate copolymer, hydroxypropyltrimonium hyaluronate, inositol, lactitol, maltitol, maltose, mannitol, mannose, methoxy polyethylene glycol, myristamidobutyl guanidine acetate, polyglyceryl sorbitol, potassium pyrollidone carboxylic acid (PCA), propylene glycol, sodium pyrollidone carboxylic acid (PCA), sorbitol, sucrose, and urea.

A pharmaceutical or cosmetic composition of the disclosure comprises, for example, an inflammatory/*rosacea* inhibitory composition and a fatty alcohol, a fatty acid, an organic base, an inorganic base, a preserving agent, a wax ester, a steroid alcohol, a triglyceride ester, a phospholipid, a polyhydric alcohol ester, a fatty alcohol ether, a hydrophilic lanolin derivative, a hydrophilic beeswax derivative, a cocoa butter wax, a silicon oil, a pH balancer, a cellulose derivative, a hydrocarbon oil, or a mixture thereof. Non-limiting examples of a suitable phospholipid include lecithin and cephalin. Suitable hydrocarbon oils include, but are not limited to, palm oil, coconut oil, and mineral oil. Additional ingredients may be included in the above compositions to vary the texture, viscosity, color and/or appearance thereof, as is appreciated by one of ordinary skill in the art.

A pharmaceutical or cosmetic composition of the disclosure can be formulated as an emulsion. Either a water-in-oil or oil-in-water emulsion may be formulated. Examples of suitable surfactants and emulsifying agents include nonionic ethoxylated and nonethoxylated surfactants, abietic acid, almond oil polyethylene glycol, beeswax, butylglucoside caprate, glycol ester, alkyl phosphate, caprylic/capric triglyceride polyethylene glycol4 esters, ceteareth-7, cetyl alcohol, cetyl phosphate, corn oil polyethylene glycol esters, dextrin laurate, dilaureth-7 citrate, dimyristyl phosphate, glycereth-17 cocoate, glyceryl erucate, glyceryl laurate, hydrogenated castor oil polyethylene glycol esters, isosteareth-11 carboxylic acid, lecithin, lysolecithin, nonoxynol-9, octyldodeceth-20, palm glyceride, polyethylene glycol diisostearate, polyethylene glycol stearamine, poloxamines, potassium linoleate, raffinose myristate, sodium caproyl lactylate, sodium caprylate, sodium cocoate, sodium isostearate, sodium tocopheryl phosphate, steareths, and trideceths. Thickening agents suitable for inclusion in a composition or formulation herein include those agents commonly used in skin care preparations. More specifically, such examples include acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxyethylcellulose, hydroxypropylcellulose, hydroxpropyl starch, magnesium alginate, methylcellulose, microcrystalline cellulose, pectin, various polyethylene glycol's, polyacrylic acid, polymethacrylic acid, polyvinyl alcohol, various polypropylene glycols, sodium acrylates copolymer, sodium carrageenan, xanthan gum, and yeast beta-glucan.

Any of a variety of art-known methods can be used to administer a cathelicidin inhibitor to a subject. For example, the cathelicidin inhibitor of the disclosure can be administered parenterally by injection or by gradual infusion over time. The composition can be administered intravenously, intraperitoneally, intramuscularly, subcutaneously, intracavity, or transdermally.

Generally, the optimal dosage of the inflammatory/*rosacea* inhibitory composition will depend upon the disorder and factors such as the weight of the subject, the type and severity of *rosacea*, the weight, sex, and degree of symptoms. Nonetheless, suitable dosages can readily be determined by one skilled in the art.

An amount of a composition effective to treat *rosacea* is used in the methods of the disclosure. For example, a small amount of the composition (from about 0.1 ml to about 5 ml) is applied to exposed areas of affected skin from a suitable container or applicator, and, if necessary, the composition is then spread over and/or rubbed into the skin using the hand, finger, or other suitable device. A composition disclosed herein is typically packaged in a container that is appropriate in view of its viscosity and intended use by a subject. For example, a lotion or fluid cream may be packaged in a bottle, roll-ball applicator, capsule, propellant-driven aerosol device, or a container fitted with a manually operated pump. A cream may simply be stored in a non-deformable bottle, or in a squeeze container, such as a tube or a lidded jar.

If desired, a suitable therapy regime can combine administration of an inflammatory/*rosacea* inhibitory composition of the disclosure with one or more additional therapeutic agents (e.g., an inhibitor of TNF, an antibiotic, and the like). For example, advising the patient to avoid those stimuli that tend to exacerbate the disease—exposure to extremes of heat and cold, excessive sunlight, ingestion of hot liquids, alcohol, and spicy foods—may help. Although its mechanism of action is not clearly understood, the mainstay of treatment is the use of oral tetracycline, especially for the papular or pustular lesions. The dosage utilized is generally 250 mg every 6 hours for the first 3 to 4 weeks, followed by tapering based on clinical response. Doxycycline and minocycline (50-100 mg every 12 hours) are also effective and have the advantage of less frequent dosage and less concern over problems with gastrointestinal absorption. Patients who are intolerant to the tetracyclines may benefit from the use of erythromycin. Oral isotretinoin, in doses similar to those used for acne vulgaris, has also been effective for the inflammatory lesions, erythema, and rhinophyma. Other oral agents that have been used include ampicillin and metronidazole. Clonidine may also be of some value in reducing facial flushing. Topical therapy for rosacea is generally less successful than systemic treatment, although often tried first. Metronidazole (2-methyl-5-nitroimidazole-1-ethanol) may be effective topically; it is available commercially as a 0.75% gel and, when applied twice daily, substantially reduces inflammatory lesions; it is classified as an antiprotozoal. Although topical corticosteroid may effectively improve signs and symptoms, long-term therapy is not advisable since it may cause atrophy, chronic vasodilation, and telangiectasia formation. The treatment of chronic skin changes may require surgical intervention.

A therapeutic objective of the methods described herein will be to reduce the severity of, or onset of, rosacea. When used to prevent rosacea optimal dosages will be based upon the results of animal studies, e.g., such as those described herein, and clinical studies performed using methods well known in the art. Mast cell stabilizing drugs are already available for the treatment of other conditions, particularly allergies, and existing dosages may serve as a starting point for evaluating dosages effective in preventing or treating rosacea. Based upon existing knowledge, it is expected that, using oral delivery methods, a patient will typically receive an oral dose of between 50 and 1500 mg of mast cell stabilizer per day, usually divided into at least two equal doses. When drug is administered topically, it is expected that an amount of between 5 and 100 mg of stabilizer will be administered each day, again with this amount being divided into several equal doses.

As described previously, the pharmaceutical compositions containing mast cell stabilizers may be placed in a finished pharmaceutical container and sold along with instructions to physicians or patients regarding the use of the compositions.

Instructions concerning the use of pharmaceutical compositions may be included on the container with the pharmaceutical composition or as a package insert. Alternatively, the instructions may be included on a box or other package in which the pharmaceutical composition is sold. In all cases, the instructions will indicate that the pharmaceutical compositions are to be administered for the purpose of treating rosacea or symptoms of rosacea. A description of the active ingredient(s) will also be included along with information concerning dosage and how the pharmaceutical composition should be administered.

The disclosure also includes methods that utilize a composition described herein to treat rosacea comprising contacting the skin with a composition of the disclosure. The compositions are typically applied topically to human skin. Accordingly, such a composition is formulated, in a further embodiment, as a liquid, cream, gel, oil, fluid cream or milk, lotion, emulsion, or microemulsion. In a related embodiment, the composition further comprises an excipient adapted for application to the face and neck. Such an excipient should have a high affinity for the skin, be well tolerated, stable, and yield a consistency that allows for easy and pleasant utilization.

The term "contacting" refers to exposing a cell or subject to a rosacea inhibitor composition such that cathelicidin production or expression is inhibited or reduced or proteases necessary for activation of cathelicidin to produce LL-37 are inhibited or reduced. Contacting can occur in vivo, for example by administering the composition to a subject afflicted with a rosacea. In vivo contacting includes both parenteral as well as topical. "Inhibiting" or "inhibiting effective amount" refers to the amount of an inflammatory/rosacea inhibitory composition that is sufficient to cause, for example, a decrease in cathelicidin production or activity, protease production or activity, or a reduction in symptoms associated with rosacea (e.g., preventing or ameliorating a sign or symptoms of a disorder such as a rash, sore, and the like) as compared to a control subject or sample.

Mast cell stabilizers and inhibitors of neuropeptides are shown herein to play a major role in the direct inactivation of the mediators of inflammation. A cocktail of mast cell stabilizers and/or neuropeptide inhibitors, their analogs, salts or derivatives, can be used alone or in combination with a corticosteroid or other active agents used to treat rosacea. The inflammatory/rosacea inhibitory composition(s), other therapeutic agents, and/or antibiotic(s) can be administered, simultaneously, but may also be administered sequentially.

The following examples are meant to illustrate the invention and are not meant to limit the foregoing disclosure or the appended claims.

EXAMPLES

The fluorogenic MMP substrate FS-6 and 6-Amidino-2-naphthy-4-guanidinobenzoate dimethanesulfonate were purchased from Enzo Life Sciences (Plymouth Meeting, Pa.). Cromolyn sodium and substance P fragment were purchased from Sigma-Aldrich (St Louis, Mo.). Adrenomedullin-2 and PACAP were purchased from AnaSpec (Fremont, Calif.). 4-methylumbelliferyl-2-acetamide-2-deoxy-b-D-glucopyranoside was purchased from Calbiochem (EMD Millipore; Billerica, Mass.). MMP-9 specific inhibitor Iand Pierce BCA protein assay kit were purchased from Thermo Fisher Scientific (Chicago, Ill.).

2 mm skin biopsies were taken from the faces of healthy and rosacea subjects, as well as tape strips from the face of erythematotelangiectatic rosacea subjects in the dermatology clinic at the University of California, San Diego. All the procedures involving human subjects were approved by the University of California San Diego Institutional Review Board under the IRB number 071032. Ten randomized adults with erythematotelangiectatic rosacea were applied a water-based solution containing either 4% cromolyn sodium or placebo, topically to their face twice a day, for 8 weeks. A clinical evaluation was performed at each visit. A total six tape strips were obtained from right and left cheek at each of the first visit and the final visit.

Mast cell deficient (C57BL/6-KitWsh$^{-/-}$) mice were bred. KitWsh$^{-/-}$ mice bearing the W-sash (Wsh) inversion mutation have MC deficiency, but lack anemia and sterility. Adult KitWsh$^{-/-}$ mice had a profound deficiency in MCs in all tissues examined, but normal levels of major classes of other differentiated lymphoid cells. Wild type mice (C57BL/6) were utilized as control. Mice were shaved 24 hrs before intradermal injection with 50 μl of 50 μM or 320 μM of Cath LL-37 or filtered PBS (n=3), twice a day for 2 days and skin biopsies were taken after 72 hours of observation. Total RNA was extracted and purified by RNeasy Mini Kit (QIAGEN science). For the time course observation, skin biopsies of WT and MC deficient mice were taken at 1, 4, and 24 hrs after Cath LL-37 injection.

For the neuropeptide experiment, 100 μL of 1 μM neuropeptide or PBS was injected into mice intradermally. Skin biopsies were taken 6 hrs after injection.

For the MC stabilizer experiment: Cromolyn sodium (0.3 mg/mouse/day) (Sigma-Aldrich, St Louis, Mo.) in PBS was injected I.P. into WT mice for 4 days.

Primary MCs were generated from mouse bone marrow and cultured as previously written (Wang et al., 2011). MCs were cultured in Stemline® II Hematopoietic Stem Cell Expansion Medium (Sigma-Aldrich).

BMMC reconstitution in KitWsh-/- mice. $4 \times 10^6$ cells of C57BL/6 mature BMMCs were diluted in filtered PBS and injected into the shaved back skin of 6 week old C57BL/6-KitWsh$^{-/-}$ mice (400 μl; 8×50 μl injections) intradermally. After 6 weeks, MCs were confirmed as resident cells in skin by toluidine blue staining.

Total-MMP activities were determined by following previously reported study (Kanada et al., 2012). To determine MMP-9 activity, MMP-9 specific inhibitor I (Thermo Fisher Scientific, Chicago, Ill.) was used.

cDNA was synthesized from RNA using the iScript cDNA Synthesis Kit (BioRad, Hercules, Calif.) according to the manufacturer's protocol. cDNA was normalized using a NanoDrop spectrophotometer (Thermo Fisher Scientific Inc.). Probes from TaqMan Gene Expression Assays (Applied Biosystems ABI, Foster City, Calif.) were used to analyze gene expressions with following to the manufacturer's instructions. Gapdh mRNA was used as an internal control to validate RNA for each sample. mRNA expression was calculated as the relative expression to Gapdh mRNA, and all data are presented as fold change of each control.

Degranulation percentage was assessed by measuring the activity of β-hexosaminidase in the supernatants as previously described (Wang et al., 2012).

ELISA (ELISA MAX™ Deluxe; BioLegend, San Diego, Calif.) was utilized to determine mouse IL-6 according to the manufacturer's instructions, normalized to total protein content.

Fluorescence immunohistochemistry. Mouse skin frozen sections were fixed with acetone, washed in 1×PBS, blocked with 5% goat serum/1% BSA for 30 minutes, and incubated with anti-MMP-9 polyclonal antibody (ABBIOTEC, San Diego, Calif.). For FcεRI detection, anti-mouse FcεRI PE (eBioscience, San Diego, Calif.) was used. Images were obtained using a Zeiss LSM510 laser scanning confocal microscope coupled with an Axiovert 100 inverted stage microscope.

Statistical analyses. The data are presented as means ±SEM. To determine the significance between two or more groups, one-way and two-way ANOVA or the two-tailed t test was used and analyzed by GraphPad Prism4 (GraphPad Software, Inc.). For all statistical tests, $p<0.05$ was considered statistically significant.

Figures 1A, 1B:
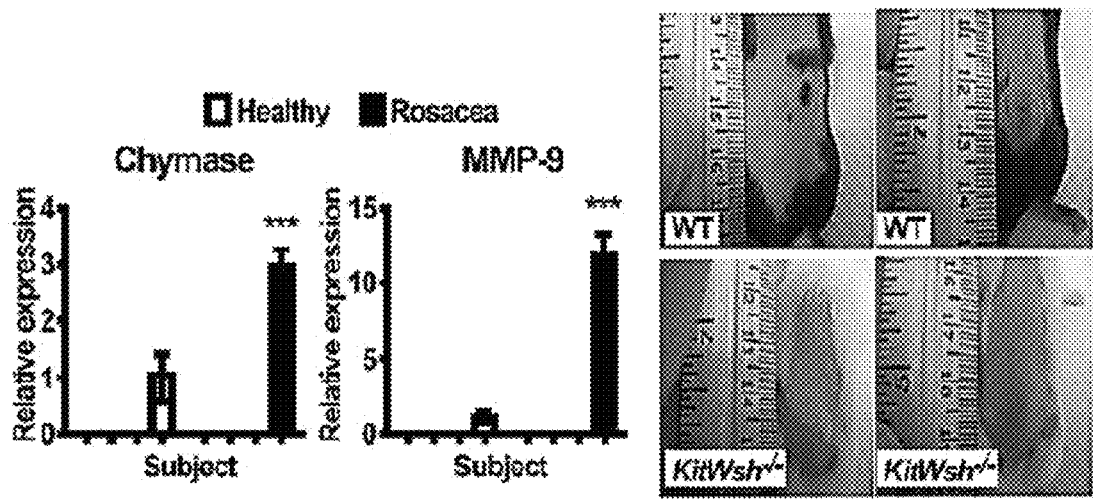
FIG. 1A-E shows mast cell (MC) proteases and MMP-9 are crucial for *rosacea* inflammation development. (a)

To verify that abnormally high Cath LL-37 is expressed in human rosacea skin, samples from 6 rosacea patients and 6 healthy control volunteers were taken and the expressions of chymase and Mmp-9 mRNAs were measured as essential markers of mast cell presence and activation (Tchougounova et al., 2005). Both chymase and Mmp-9 mRNA levels showed significant increases in rosacea skin compared with healthy skin (n=6) (FIG. 1a). Meaning that MCs were abnormally activated and were specifically expressing enzymes involved in Cath LL-37 processing.

Figures 1C, 1D:
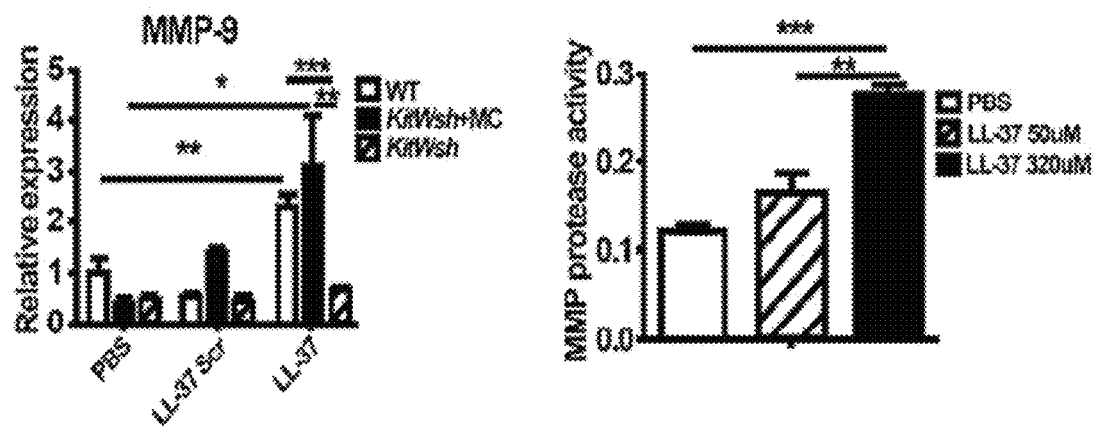
Figure 1E:
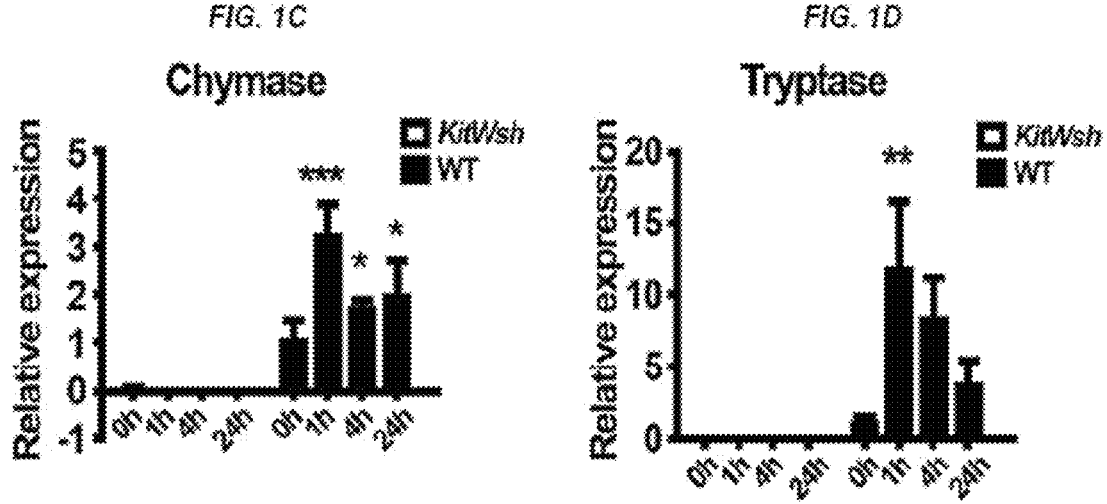

To prove that MCs are central to the pathogenesis of rosacea, a well-established mouse model of rosacea-like inflammation was used (Yamasaki et al., 2007). Cath LL-37 was injected intradermally into mast cell deficient mice (KitWsh$^{-/-}$) and compared the resulting inflammation with Wild Type (WT) mice. The clinical end point observation (at 72 hrs) showed rosacea-like inflammation in the skin of WT mice injected with Cath LL-37, whereas KitWsh$^{-/-}$ mice did not develop any rosacea-like features (FIG. 1b). In order to further establish the essential role of mast cells in the observed phenotype, the mast cells from deficient mice were reconstituted with wild type mast cells and repeated the injections with Cath LL-37. To define the specificity of Cath LL-37 in mast cell activation, a Cath LL-37 scrambled peptide was also included in the experiments. The results showed that, following Cath LL-37 challenge, Mmp-9 mRNA expression in skin from MC deficient mice was significantly lower than in skin from WT ($p<0.01$) and WT MC-reconstituted KitWsh$^{-/-}$ mice ($p<0.05$). There was no significant difference observed between any of the mouse groups when Cath LL-37 scrambled peptide was used (FIG. 1c). Different concentrations (50 μM and 320 μM) of Cath LL-37 peptide were also injected into WT mice and demonstrated that Cath LL-37 induced MMP activity increases in a dose dependent manner in WT mice (FIG. 1d). Furthermore, a time course experiment showed that the chymase and tryptase were expressed immediately after injection of Cath LL-37, while the same enzymes were not detectable in the skin of the MC-deficient mice (FIG. 1e).

Figure 2A:
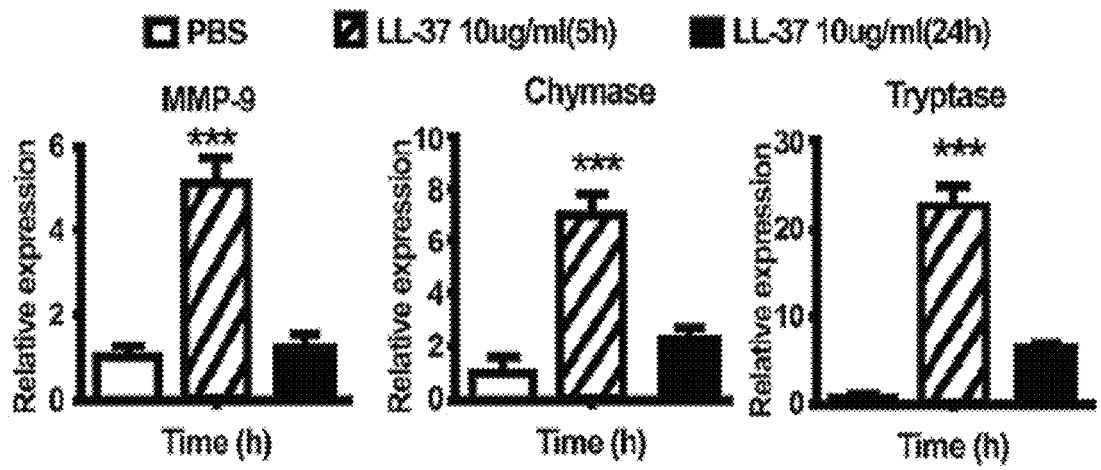
Figure 2B:
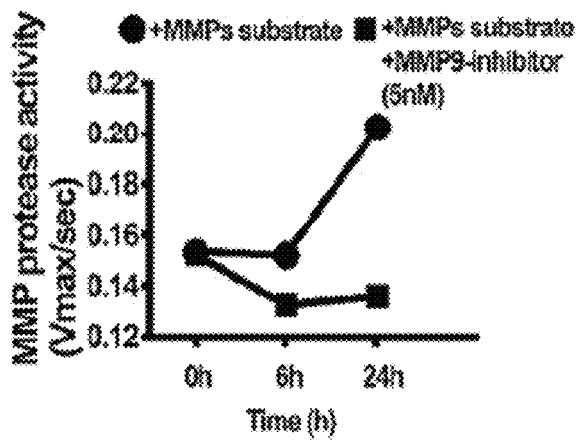
Figure 2C:
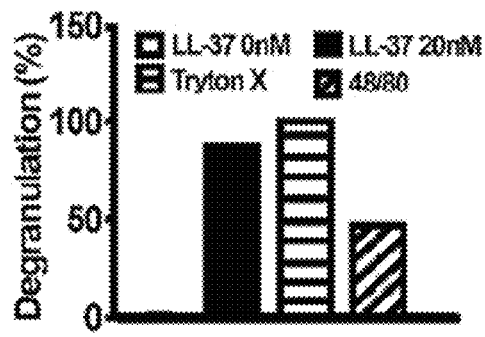
Figure 2D:
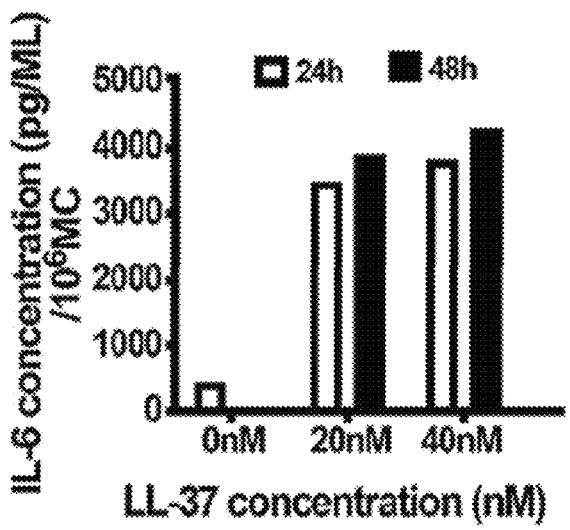
Figure 2E:
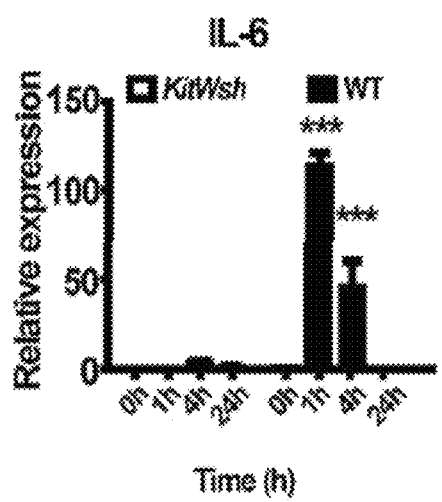

To confirm that mast cells are responsive to direct Cath LL-37 stimulation, bone marrow derived mouse MCs were stimulated with different concentrations of Cath LL-37 at different time points. Tryptase, chymase, and Mmp-9 mRNA expressions were significantly higher at 5 hrs ($p<0.001$) (FIG. 2a), while Mmp-1a, Klk5, and Klk6 were not detectable at 5 hrs. MMP-9 protease activity in the culture medium of MCs stimulated with Cath-LL37 for 24 hrs was confirmed by fluorescence enzymatic activity assay using an MMP specific substrate and an MMP-9 specific inhibitor (FIG. 2b). MC degranulation was confirmed by measuring β-hexosaminidase release in Cath LL-37 stimulated MC supernatants. A low concentration of Cath LL-37 (20 nM) was shown to be able to induce degranulation (FIG. 2c). In addition, high levels of secreted IL-6 were detected by ELISA in mouse MCs after 24 and 48 hrs of stimulation with different Cath LL-37 concentrations (20 nM and 40 nM) (FIG. 2d). Increased IL-6 mRNA expression was also observed in skin from WT mice, but not in mast cell deficient mice, following Cath LL-37 challenge (FIG. 2e).

Rosacea flare-ups are frequently initiated by face flushing due to neuronal dysfunction and increased release of pituitary adenylate cyclase-activating peptide (PACAP) (Schwab et al., 2011). To investigate whether neuropeptides (NPs) require MC activation for the development of the inflammatory response in rosacea, 100 μL of 1 μM NP (substance P: SP, adrenomedullin-2: ADM-2, PACAP) was injected intradermally into WT and MC deficient mice. Tryptase mRNA expression was observed to be dramatically increased by PACAP stimulation ($p<0.01$) in WT mice. Chymase, Mmp-1 and Mmp-9 were only significantly increased ($p<0.05$) in WT mice (FIG. 3a) only when stimulated with PACAP. In addition, mRNA expressions of the pro-inflammatory cytokines Cxcl2 and Tnf-α were also significantly increased with PACAP challenge in WT mice, but not in MC deficient mice (p<0.01) (FIG. 3b). These results prove that neurovascular alteration and neuropeptide release during a face flushing can be translated to *rosacea* inflammation in skin through the activation of MC enzymes. Moreover, these same MC enzymes can further increase the levels of free Cath LL-37 and amplify the inflammatory response.

According to the obtained results, MC proteases and MMP-9, which are released from MCs upon stimulation by Cath LL-37, are central in promoting *rosacea*-like skin inflammation. Therefore, it was hypothesized that blocking MC degranulation would also prevent the formation of *rosacea*-like inflammation in the skin. To test this hypothesis, cromolyn sodium, a very well-known MC stabilizer, was injected I.P. into WT mice (10 mg/kg, per day) every day for 4 days before Cath LL-37 challenge. 24 hours after the last cromolyn sodium injection, mice were injected with 50 µl of 320 µm Cath LL-37 or PBS, twice a day for 2 days. As expected, skin inflammation did not develop in the mice pretreated with cromolyn. Mmp-9 and Cxcl2 expressions were significantly decreased in the cromolyn treated mice (p<0.01) (FIG. 4a). Consistent with Mmp-9 mRNA expression, MMP-9 activity in the tissue was also dramatically decreased by cromolyn pretreatment (p<0.01) (FIG. 4b). In addition, frozen skin sections were stained with anti-MMP-9 and anti-FcεRI antibodies for the detection of MCs. The immunostaining showed that numerous MMP-9 positive MCs were observed in Cath LL-37 treated mice, but not in cromolyn pretreated Cath LL-37 mice (FIG. 4c).

Because we wanted to understand how human keratinocytes respond to human MCs, co-cultures of normal human epidermal keratinocytes (NHEK) cells with supernatant from human cord blood-derived MCs which had been degranulated by compound 48/80 were analyzed. MMP and KLK activities were significantly increased in NHEK cells when cells were co-cultured for 24 hrs with 100 µL of MC supernatant (p<0.001) (FIGS. 5a and b). Since the activation of cathelicidin in keratinocytes requires the active form of vitamin D3, 1,25(OH)2VD3 (Schauber et al., 2007), we also added 1,25(OH)2VD3 in the co-culture model. Cath LL-37 mRNA level was significantly increased after co-culture with MC supernatant (p<0.001) (FIG. 5b). This confirmed that, while LL-37 activate MCs, MC proteases increase LL-37 production in human skin epidermis, amplifying the inflammation and creating a vicious cycle.

To test whether the results were reproducible in humans, 10 randomized adults with erythematotelangiectatic *rosacea* were used to apply a solution containing either the MC stabilizer (4% cromolyn sodium) or placebo, topically to their face twice daily. Six tape strips were obtained from both right and left cheeks, at the time of first visit (v1) and last visit (v4). After eight week (v4), facial erythema levels decreased in the cromolyn treatment group. MMP, KLK activity and Cath LL-37 protein levels were decreased in the cromolyn treatment group with significant activity in MMP observed (FIG. 5c).

Many MC functions, mediated by MC proteases, have been identified as mediators of skin disease inflammation and, therefore, should be considered targets for future therapeutics. An abnormal increase in the free form of hCAP18 (Cath LL-37) antimicrobial peptide in human skin is a key part of the pathogenesis of *rosacea*. MCs are one of the primary sources of cathelicidin in the skin and they are also the main source of enzymes that activate cathelicidin to its active form (Cath LL-37). Previous studies have reported that MCs are increased in the skin of *rosacea* patients (Yamasaki et al., 2007). However, a great number of questions remain regarding the manner in which inflammatory signals are transmitted from the epidermis to vessels and inflammatory cells. The disclosure demonstrates that MC proteases and Mmp-9 mRNAs are highly expressed in skin from *rosacea* patients (FIG. 1a). The disclosure further demonstrates that after Cath LL-37 has been released from the epidermis in *rosacea* skin, it in turn activates MCs to induce inflammation and neutrophil recruitment, which results in more Cath LL-37.

The disclosure demonstrates that Cath LL-37 peptide strongly activates skin MCs to release proteases that are crucial in the development of *rosacea*-like inflammation in vivo. The data showed that in MC-deficient mice, intradermal Cath LL-37 injections did not generate all of the dermal events that are usually found in *rosacea*, including inflammation and MMP-9 activation. To strongly support this hypothesis that mast cells are crucial in the generation of skin inflammation, when reconstituted mast cell deficient mice were injected with WT mast cells the *rosacea*-like inflammation phenotype reappears. Moreover, the data demonstrated the specificity of Cath LL-37 peptide in mast cell activation by showing that injection of a scrambled peptide did not induce inflammation (FIG. 1c). This result is nicely paralleled by our in vitro experiments, where we observed an increase in MMP-9 protease activity in the culture supernatant of Cath LL-37 treated bone marrow MCs (FIG. 1d). The hypothesis that MMP-9 is involved in *rosacea* pathogenesis is supported by the recent discovery that doxycycline, which is an effective therapeutic for improving *rosacea* symptoms, inhibits MMPs directly (Kanada et al., 2012). Accordingly, any composition of the disclosure can include a combination of a mast cell stabilizer and doxycycline.

Furthermore, any signal (especially from neurogenic factors) that induces the activation of MCs results in the amplification of the inflammatory response, thus it is propose that MCs are the missing link between flaring and inflammation in *rosacea*. Tryptase activates PAR-2 on nerve endings and keratinocytes, which in turn causes the release of neuropeptides. On the other hand, activated PAR-2 stimulates MC mediator release (e.g. histamine release) during cutaneous inflammation. Activated PAR-2 enhances these receptors in the vascular endothelial cells and immune cells (Aubdool and Brain, 2011), explaining how MCs might be linked to *rosacea* flashing and erythema. PACAP is a neuropeptide that has been shown to be one of the main mediators in the response to psychological stress and is abundantly expressed in *rosacea*-affected skin (Schwab et al., 2011). It has been reported that PACAP is not only able to induce neuronal inflammation, but also edema and flushing in human skin (Roosterman et al., 2006). Dramatically increased expressions of the pro-inflammatory cytokines Tnf-α and Cxcl2 were observed in skin after PACAP challenge (FIGS. 3a and b). Though it is well known that neuronal activation results in the release of mast cell-derived histamine and leukotriene, the data presented here confirms that PACAP increases the expressions of Mmp-1 and Mmp-9, which are activators of hCAP18 processing to Cath LL-37. The data also showed that activated mast cells, release enzymes that increase LL-37 expression in keratinocytes. Thus, a link between PACAP and Cath LL-37 is demonstrated. Consequently, these peptides work synergistically in the development of *rosacea* symptoms in human skin.

The data also show that mice injected I.P. with cromolyn did not develop *rosacea*-like skin inflammation after Cath LL-37 challenge. Moreover, MMP-9 activity, Mmp-9 and Cxcl2 and MMP-9/MC immunostaining in the skin were significantly decreased compared with mice not treated with cromolyn. Cxcl2 is the mouse homolog of human IL-8 and is crucial for neutrophil recruitment in vivo.

From the results presented here, MC stabilizers actually block MC induced inflammation and have the potential to be developed as therapeutics for the treatment of *rosacea*. MMPs are known to be involved in angiogenesis and apoptosis (Amalinei et al., 2010). Chymase, a MC specific protease, can not only activate pro-MMP-9 and other MMP cascades (Tchougounova et al., 2005), but can also inhibit enzyme degradation by TIMP-1. The data show that pro-inflammatory peptides generated from epidermal keratinocytes and sensory nerve endings, activate dermal mast cells, that in turn amplify skin inflammation and angiogenesis via their secretion of proteases, MMP-9, and pro-inflammatory cytokines. In addition, the in vitro data of NHEK cells strongly support the hypothesis that protease generated from MCs will induce dermal inflammation and increase the production of enzymes from the epidermal layer able to generate LL-37, with the result of creating a pro-inflammatory loop (FIGS. 5a and b). Release of MMP-9 activates KLKs, which results in the generation of additional active Cath LL-37 peptide (FIG. 6).

The experiments here shows that *rosacea* features cannot be generated in mouse skin in the absence of MCs or when MCs have been pharmacologically stabilized. LL-37 and neuropeptides activate MCs; activated human MC, in turn, increase NHK expression and processing of LL-37, making human MCs central in amplifying *rosacea* inflammation and symptoms, especially erythema, flushing and telangiectasia. Moreover, the results on a limited clinical trial, supports the hypothesis that MC stabilizers improve *rosacea* outcome in humans.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method of treating *rosacea* comprising contacting a subject having *rosacea* with a composition comprising a mast cell stabilizer, a serine protease inhibitor, and an agent that inhibits a neuropeptide selected from the group consisting of substance P (SP), calcitonin gene-related peptide (CGRP), vasoactive intestinal peptide (VIP), neurokinin A (NKA), pituitary adenylate cyclase-activating peptide (PACAP), and any combination thereof, wherein the mast cell stabilizer is selected from the group consisting of lodoxamide, nedocromil, cromolyn, pemirolast, pharmaceutical salts thereof, and any combination thereof, wherein the serine protease inhibitor is selected from the group consisting of Cystatin, aprotinin, 4-(2-aminoethyl)-benzenesulfonylfluoride, aminocaproic acid, kunitz-type protease inhibitor, amyloid beta protein precursor, TFPI (Tissue Factor Pathway Inhibitor), collagen alpha 3, collagen alpha 3 (VI) chain precursor, HKIB9 (Human Kunitz-type Inhibitor type 9), ITI-KD1 (Inter-Trypsin Inhibitor, Kunitz Domain 1), ITI-KD2 (Inter-Trypsin Inhibitor, Kunitz Domain 2), chelonianin, Beta-1-Bungarotoxin B chain, snake venom protease inhibitors, and any combination thereof, and wherein the composition reduces the production of a peptide comprising amino acid 134 to amino acid 170 of SEQ ID NO:2 in the subject.

2. The method of claim 1, wherein the composition reduces the production of one or more proteases selected from the group consisting of chymase, tryptase, MMP-1, and MMP-9 in the subject.

3. The method of claim 1, wherein the serine protease inhibitor comprises Cystatin, aprotinin, 4-(2-aminoethyl)-benzenesulfonylfluoride, aminocaproic acid and any combination thereof.

4. The method of claim 1, wherein the serine protease inhibitor inhibits kallikrein SCTE.

5. The method of claim 1, further comprising contacting the subject with a vitamin D receptor inhibitor.

6. The method of claim 1, wherein the contacting is by topical application.

7. The method of claim 5, wherein the vitamin D receptor inhibitor comprises 6-fluoro-vitamin D3 (6-F-D3).

8. The method of claim 1, wherein the composition is formulated for topical administration.

9. The method of claim 8, wherein the composition comprises a sugar, polysaccharide, sugar alcohol or an oil.

10. The method of claim 9, wherein the sugar, polysaccharide, sugar alcohol, or oil comprises one or more of lactose, 1,2-propylene glycol, a polygycol, a fatty alcohol, dextrose, glucose, glycogen, a glycolipid, glycerin, tocopheryl glucoside, inositol, lactitol, maltitol, maltose, mannitol, mannose, methoxy polyethylene glycol, polyglyceryl sorbitol, sorbitol, sucrose, vegetable oil, ethyl oleate, jojoba oil, avocado oil, sunflower seed oil, lanosterol, linoleic acid, linolenic acid, a phytosterol, a placental lipid, *Vitis vinifera* seed oil, a sphingolipid, stearamidopropylbetaine, stearyl palmitate, tocopherol, tocopheryl acetate, tocopheryl linoleate, mineral oil, petrolatum, acetylated lanolin, apricot kernel oil, butoxyethyl stearate, ethylhexyl myristate, glyceryl isostearates, glyceryl oleate, hexyldecyl stearate, hexyl isostearate, hydrogenated palm glycerides, hydrogenated soy glycerides, hydrogenated tallow glycerides, isostearyl neopentanoate, isostearyl palmitate, isotridecyl isononanoate, laureth-2 acetate, lauryl polyglyceryl-6 cetearyl glycol ether, methyl gluceth-20 benzoate, mineral oil, myreth-3 palmitate, octyldecanol, octyldodecanol, *odontella aurita* oil, 2-oleamido-1,3 octadecanediol, polyethylene glycol castor oil, palm oil, coconut oil, beeswax, corn oil, sodium caproyl lactylate, sodium caprylate, sodium cocoate, sodium isostearate, sodium tocopheryl phosphate, steareths, ceramides, ceteareth-7, cetyl alcohol, glyceryl isostearate, propylene glycol, silicon oil, or trideceths or any combination thereof.

11. The method of claim 8, wherein the composition is formulated in petrolatum, sorbitol, and/or propylene glycol.

12. The method of claim 1, wherein the composition comprises a skin lightening agent, a sunscreen agent, a skin conditioning agent, a skin protectant, an emollient, a humectant, or any combination thereof.

13. The method of claim 1, wherein the composition further comprises a matrix metalloproteinase inhibitor.

\* \* \* \* \*

SEQUENCE LISTING

```
<160> NUMBER OF SEQ ID NOS: 2

<210> SEQ ID NO 1
<211> LENGTH: 739
<212> TYPE: DNA
<213> ORGANISM: Homo sapiens
<220> FEATURE:
<221> NAME/KEY: CDS
<222> LOCATION: (141)..(653)

<400> SEQUENCE: 1
taaagcaaac cccagcccac accctggcag gcagccaggg atgggtggat caggaaggct      60
cctggttggg cttttgcatc aggctcaggc tgggcataaa ggaggctcct gtgggctaga     120
gggaggcaga catggggacc atg aag acc caa agg gat ggc cac tcc ctg ggg    173
                        Met Lys Thr Gln Arg Asp Gly His Ser Leu Gly
                         1               5                  10 cgg tgg tca ctg gtg ctc ctg ctg ggc ctg gtg atg cct ctg gcc           221
Arg Trp Ser Leu Val Leu Leu Leu Gly Leu Val Met Pro Leu Ala
             15                  20                  25 atc att gcc cag gtc ctc agc tac aag gaa gct gtg ctt cgt gct ata       269
Ile Ile Ala Gln Val Leu Ser Tyr Lys Glu Ala Val Leu Arg Ala Ile
         30                  35                  40 gat ggc atc aac cag cgg tcc tcg gat gct aac ctc tac cgc ctc ctg       317
Asp Gly Ile Asn Gln Arg Ser Ser Asp Ala Asn Leu Tyr Arg Leu Leu
     45                  50                  55 gac ctg gac ccc agg ccc acg atg gat ggg gac cca gac acg cca aag       365
Asp Leu Asp Pro Arg Pro Thr Met Asp Gly Asp Pro Asp Thr Pro Lys
 60                  65                  70                  75 cct gtg agc ttc aca gtg aag gag aca gtg tgc ccc agg acg aca cag       413
Pro Val Ser Phe Thr Val Lys Glu Thr Val Cys Pro Arg Thr Thr Gln
                 80                  85                  90 cag tca cca gag gat tgt gac ttc aag aag gac ggg ctg gtg aag cgg       461
Gln Ser Pro Glu Asp Cys Asp Phe Lys Lys Asp Gly Leu Val Lys Arg
             95                 100                 105 tgt atg ggg aca gtg acc ctc aac cag gcc agg ggc tcc ttt gac atc       509
Cys Met Gly Thr Val Thr Leu Asn Gln Ala Arg Gly Ser Phe Asp Ile
        110                 115                 120 agt tgt gat aag gat aac aag aga ttt gcc ctg ctg ggt gat ttc ttc       557
Ser Cys Asp Lys Asp Asn Lys Arg Phe Ala Leu Leu Gly Asp Phe Phe
    125                 130                 135
```

```
cgg aaa tct aaa gag aag att ggc aaa gag ttt aaa aga att gtc cag     605
Arg Lys Ser Lys Glu Lys Ile Gly Lys Glu Phe Lys Arg Ile Val Gln
140             145                 150                 155 aga atc aag gat ttt ttg cgg aat ctt gta ccc agg aca gag tcc tag     653
Arg Ile Lys Asp Phe Leu Arg Asn Leu Val Pro Arg Thr Glu Ser
                160                 165                 170 tgtgtgccct accctggctc aggcttctgg gctctgagaa ataaactatg agagcaattt   713
caaaaaaaaa aaaaaaaaaa aaaaaa                                        739

<210> SEQ ID NO 2
<211> LENGTH: 170
<212> TYPE: PRT
<213> ORGANISM: Homo sapiens

<400> SEQUENCE: 2

Met Lys Thr Gln Arg Asp Gly His Ser Leu Gly Arg Trp Ser Leu Val
1               5                   10                  15

Leu Leu Leu Leu Gly Leu Val Met Pro Leu Ala Ile Ile Ala Gln Val
                20                  25                  30

Leu Ser Tyr Lys Glu Ala Val Leu Arg Ala Ile Asp Gly Ile Asn Gln
            35                  40                  45

Arg Ser Ser Asp Ala Asn Leu Tyr Arg Leu Leu Asp Leu Asp Pro Arg
    50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Phe Arg Lys Ser Lys Glu
    130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170
```